(12) United States Patent
Mozaffarian et al.

(10) Patent No.: US 10,371,702 B2
(45) Date of Patent: Aug. 6, 2019

(54) DETECTION AND TREATMENT OF AUTOIMMUNE DISORDERS

(71) Applicant: Seattle Children's Hospital, Seattle, WA (US)

(72) Inventors: Neelufar Mozaffarian, Mercer Island, WA (US); Anne M. Stevens, Seattle, WA (US)

(73) Assignee: SEATTLE CHILDREN'S HOSPITAL, Seattle, WA (US)

(*) Notice: Subject to any disclaimer, the term of this patent is extended or adjusted under 35 U.S.C. 154(b) by 345 days.

(21) Appl. No.: 14/874,851

(22) Filed: Oct. 5, 2015

(65) Prior Publication Data

US 2016/0131646 A1 May 12, 2016

Related U.S. Application Data

(63) Continuation of application No. 13/630,364, filed on Sep. 28, 2012, now Pat. No. 9,168,296, which is a continuation of application No. 13/282,334, filed on Oct. 26, 2011, now abandoned, which is a continuation of application No. 12/243,913, filed on Oct. 1, 2008, now Pat. No. 8,062,852.

(60) Provisional application No. 60/997,334, filed on Oct. 1, 2007.

(51) Int. Cl.
| | |
|---|---|
| C07K 16/28 | (2006.01) |
| G01N 33/564 | (2006.01) |
| A61K 38/06 | (2006.01) |
| A61K 38/07 | (2006.01) |
| A61K 31/713 | (2006.01) |
| A61K 39/395 | (2006.01) |

(52) U.S. Cl.
CPC ......... *G01N 33/564* (2013.01); *A61K 31/713* (2013.01); *A61K 38/06* (2013.01); *A61K 38/07* (2013.01); *A61K 39/3955* (2013.01); *C07K 16/2803* (2013.01); *C07K 2317/76* (2013.01); *G01N 2333/70503* (2013.01); *G01N 2800/102* (2013.01); *G01N 2800/104* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 4,402,934 A * | 9/1983 | Teodorescu | ......... | G01N 33/564 435/2 |
| 4,645,748 A * | 2/1987 | Hurwitz | ............ | C07K 14/4713 436/509 |
| 6,159,748 A * | 12/2000 | Hechinger | .......... | C12Q 1/6816 435/5 |
| 6,555,320 B1 * | 4/2003 | Goronzy | .............. | G01N 33/564 424/130.1 |
| 6,843,990 B2 * | 1/2005 | Shen-Chih | ......... | C07K 16/2878 424/130.1 |
| 7,445,903 B2 * | 11/2008 | Serre | ................... | C07K 14/4713 435/7.1 |
| 7,534,605 B2 * | 5/2009 | Naor | ................ | C07K 14/70585 424/143.1 |
| 7,588,905 B2 * | 9/2009 | Ahearn | ................ | G01N 33/564 435/287.2 |
| 8,062,852 B2 | 11/2011 | Mozaffarian et al. | | |
| 9,168,296 B2 * | 10/2015 | Mozaffarian | ......... | A61K 38/06 |
| 2002/0102651 A1 | 8/2002 | Freeman et al. | | |
| 2009/0028875 A1 * | 1/2009 | Emilie | ................... | A61K 39/35 424/172.1 |
| 2009/0055944 A1 * | 2/2009 | Korman | ................ | C07K 16/28 800/18 |
| 2009/0215084 A1 * | 8/2009 | Kwon | .............. | G01N 33/57484 435/7.21 |
| 2009/0304735 A1 * | 12/2009 | Belz | ..................... | A61K 39/385 424/199.1 |

OTHER PUBLICATIONS

Merriam-Webster Dictionary, accessed online at https://www.merriam-webster.com/dictionary/correlation on Oct. 10, 2017; 1 page.*
Johnson et al. Front Immunol. 2017; vol. 8, Article 961 (pp. 1-9).*
Uzzaman et al. Allergy Asthma Proc. 2012; 33: S96-S99.*
Du et al. Journal of Oral Pathology and Medicine (2011) 40: 525-532.*
Albert et al, Immature dendritic cells phagocytose apoptotic cells via alphav beta5 and CD36, and cross-present antigens to cytotoxic T lymphocytes, J Exp Med, (1998), 188(7):1359-1368.
Avarado-Sánchez et al, Regulatory T cells in patients with systemic lupus erythematosus, J Aut, (2006), 27:110-118.
Blanco et al, Induction of dendritic cell differentiation by INF-alph in systemic lupus erythematosus, Science, (2001), 294:1540-1543.
Brown et al, Blockade of Programmed Death-1 Ligands on Dendritic Cells Enhances T Cell Activation and Cytokine Production, The Journal of Immunology, (2003), 170:1257-1266.
Butte et al, PD-L1 interacts specifically with B7-1 to inhibit T cell proliferation, Immunity, (2007), 27(1):111-112.
Carter et al, PD-1/PD-L1, but not PD-1/Pd-L2, interactions regulate the severity of experimental autoimmune encephalomyelitis, Journal of Neuroimmunology, (2007), 182:124-134.
Chen et al, Expression of programmed-death receptor ligands 1 and 2 may contribute to the poor stimulatory potential of murine immature dendritic cells, Immunobiology, (2007), 212:159-165.
Chen et al, Increased Apoptosis of Peripheral Blood Lymphocytes and Its Association With Interleukin-18 in Patents With Active Untreated Adult-Onset Still's Disease, Arthritis & Rhematism, (2007), 57(8):1530-1538.
Decker et al, Monocyte-derived dendritic cells over-express CD86 in patients with systemic lupus erythematosus, Rheumatology, (2006), 45:1087-1095.
Ding et al, Aberrant Phenotype and Function of Myeloid Dendritic Cells in Systemic Lupus Erythematosus, Journal of Immunology, (2006), 177:5878-5889.

(Continued)

*Primary Examiner* — Ilia I Ouspenski
(74) *Attorney, Agent, or Firm* — Foley & Lardner LLP

(57) ABSTRACT

Disclosed herein are methods of treatment of autoimmune diseases such as systemic lupus erythematosus (SLE) as well as clinical assays for detection of autoimmune disease activity in patients utilizing a PD1 ligand.

18 Claims, 21 Drawing Sheets

(56) References Cited

OTHER PUBLICATIONS

Ding et al, B7H1-Ig Fusion Protein Activates the CD4plus IFN-gamma Receptor Type 1 T Regulatory Subset Through IFN-gamma-Secreting Th1 Cells, The Journal of Immunology, (2006), 177:3606-3614.

Dong et al, B7-H1, a third member of the B7 family, co-stimulates T-cell proliferation and interleukin-10 secretion, Nature America Inc., (1999), 5(12):1365.

Dong et al, Tumor-associated B7-H1 promotes T-cell apoptosis: A potential mechanism of immune evasion, Nature Medicine, (2002), 8(8):793.

Feng et al, Association of Increased Interferon-Inducible Gene Expression With Disease Activity and Lupus Nephritis in Patients With Systemic Lupus Erythematosus, Arthritis & Rheumatism, (2006), 54(9):2951-2952.

Ferreiros-Vidal et al, Association of PDCD1 With Susceptibility to Systemic Lupus Erythematosus, Arthritis & Reumatism, (2004), 50(8):2590-2597.

Fife et al, Insulin-induced remission in new-onset NOD mice is maintained by the PD-1-PD-L1 pathway, JEM, (2006), 203(12):2737-2747.

Fiore et al, Immature myeloid and plasmacytoid dendritic cells infiltrate renal tubulointerstitium in patients with lupus nephristis, Molecular Immunology, (2008), 45:259-265.

Freeman et al, Engagement of the PD-1 Immunoinhibitory Receptor by a Novel B7 Family Member Leads to Negative Regulation of Lymphocyte Activation, J Exp Med, (2000), 192(7):1027-1034.

Fukushima et al, Involvement of programmed death-ligand 2 (PD-L2) in the development of experimental allergic conjunctivitis in mice, Br J Opthalmol, (2006), 90:1040-1045.

Geng et al, B7-H1 expression is upregulated in peripheral blood CD14plus monocytes of patients with chronic hepatitis B virus infection, which correlates with higher serum IL-10 levels, Journal of Viral Hepatitis, (2006), 13:725-733.

Golden-Mason et al, Upregulation of PD-1 Expression on Circulating and Intrahepatic Hepatitis C Virus-Specifric CD8plus T Cells Associated with Reversible Immune Dysfunction, Journal of Virology, (2007), 249-9258.

He et al, Programmed death-1 ligands-transfected dendritic cells loaded with glutamic acid decarboxylase 65 (GAD65) inhibit both the alloresponse and the GAD65-reactive lymphocyte response, Clinical and Experimental Immunology, (2007), 151:86-93.

Her et al., "Increased expression of soluble inducible costimulator ligand (COSL) in patients with systemic lupus erythematosus," Lupus, vol. 18, No. 6, pp. 501-507, May 2009.

Hirata et al, Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand, The Journal of Immunology, (2005).

Hochberg et al, Polymyalgia rheumatica in patients with a normal erythrocyte sedimentation rate: comment on the artcle by Helfgott and Kieval, Arthritis & Rheumatism, (1997), 40(9): 1725-1734.

Karni et al, Innate Immunity in Multiple Sclerosis: Myeloid Dendritic Cells in Secondary Progressive Multiple Sclerosis Are Activated and Drive a Proinflammatory Immune Response, J Immuno, (2006), 177:4196-4202.

Keir et al, Tissue expression of PD-L1 mediates peripheral T cell tolerance, JEM, (2006), 203(4):883-895.

Kim et al, High-level expression of B7-H1 molecules by dendritic cells suppresses the function of activated T cells and desensitizes allergen-primed animals, Journal of Leukocyte Biology, (2006), 79:686.

Kitazawa et al, Involvement of the Programmed Death-1/Programmed Death-1 Ligand Pathway in CD4plusCD25plusRegulatory T-Cell Activity to Suppress Alloimmune Responses, Transplantation, (2007), 83:774-782.

Krishnan et al, Increased Caspase-3 Expression and Activity Contribute to Reduced CD3zeta Expression in Systemic Lupus Erythematosus T Cells, The Journal of Immunology, (2005), 175:3417-3423.

Latchman et al, PD-L1-deficient mice show that PD-L1 on T cells, antigen-presenting cells, and host tissues negatively regulates T cells, PNAS, (2004), 101(29):10691-10696.

Latchman et al, PD-L2 is a second ligand for PD-1 and inhibits T cell activation, Nature Immunology, (2001), 2(3):261-268.

Liang et al, Regulation of PD-1, PD-l1, and PD-L2 expression during normal and autoimmune responses, Eur J Immunol, (2003), 33:2706-2716.

Liu et al, Differential Expression and Modulation of Costimulatory Molecules CD80 and CD86 on Monocytes from Patients with Systemic Lupus Erythematosus, Sc and J Immunol, (1999), 49:82-87.

Martin-Orozco et al, Cutting Edge: Programed Death(PD) Ligand-1/PD-1 Interaction Is Required for CD8plus T Cell Tolerance to Tissue Antigens, The Journal of Immunology, (2006), 177:8291-8295.

Mosca et al, The validity of the ECLAM index for the retrospective evaluation of disease activity in systemic lupus erythematosus, Lupus, (2000), 9:445-450.

Nishimura et al, Development of Lupus-like Autoimmune Diseases by Disruption of the PD-1 Gene Encoding an ITIM Motif-Carrying Immunoreceptor, Immunity, (1999), 11:141-151.

Pamuk et al., "PECAM-1 gene polymorphisims and soluble PECAM-1 level in rheumatoid arthritis and systemic lupus erythematosus patients: any link with clinical atherosclerotic events?," Clin. Rheumatol. published online Sep. 10, 2014.

Probst et al, Resting dendritic cells induce peripheral CD8plus T cell tolerance through PD-1 and CTLA-4, Nature Immunology, (2005), 6(3):280.

Prokunina et al, A regulatory polymorphism in PDCD1 is associated with susceptibility to systemic lupus erythematosus in humans, Nature Genetics, (2002), 32:666.

Qin et al., "Elevated levels of serum sCXCL16 in systemic lupus erythematosus; potential involvement in cutaneous and renal manifestations," Clin. Rheumatol., published online Jul. 13, 2014.

Sakane et al, Failure of autologous mixed lymphocyte reactions between T and non-T cel s in patients with systemic lupus erythematosus, Proc Natl Acad Sci, (1978), 75(7):3464-3468.

Scheinecker et al, Initiation of the Autologous Mixed Lymphocyte Reaction Requires the Expression of Costimulatory Molecules B7-1 and B7-2 on Human Peripheral Blood Dendritic Cells, The Journal of Immunology, (1998), 161:3966-3973.

Sharpe et al, The function of programmed cell death 1 and its ligand in regulating autoimmunity and infection, Nature Immunology, (2007), 8(3):239.

Thorburn et al, Association of PDCD1 genetic variation with risk and clinical manifestations of systemic lupus erythematosus in a multiethnic cohort, Genes Immun, (2007), 8(4):279-287.

Trabattoni et al, B7-H1 is up-regulated in HIV infection and is a novel surrogate marker of disease progression, Blood, (2002), 101:2514-2520.

Tsutsumi et al, Phenotypic and genetic analyses of T-cell-mediated immunoregulation in patients with Type 1 diabetes, Diabet Med, (2006), 23:1145-1150.

U.S. Notice of Allowance dated Jun. 8, 2011 in U.S. Appl. No. 12/243,913.

U.S. Notice of Allowance dated Jul. 13, 2011 in U.S. Appl. No. 12/243,913.

Valencia et al, Deficient DC4plusDC25 high T Regulatory Cell Function in Patients with Active Systemic Lupus Erythematosus.

Velázquez-Cruz et al, Association of PDCD1 polymorphisms with childhood-onset systemic lupus erythematosus, European Journal of Human Genetics, (2007), 15:336-341.

Wang et al, Ligands for Programmed Cell Death1 Gene in Patients with Systemic Lupus Erythematosus, J Rheumato, (2007), 34:721-725.

Wang et al, Programmed Death-1 Gene Polymorphisms in Patients With Systemic Lupus Erythematosus in Taiwan, Journal of Clinical Immunology, (2006), 26:506.

(56) References Cited

OTHER PUBLICATIONS

Yu et al, Lymphopenia is associated with neuropsychiatric manifestations and disease activity in paediatric systemic lupus erythematosus patients, Rheumatology, (2007), 46:1492-1494.
Zhu et al, Differential Role of Programmed Death-Ligand 1 and Programmed Death-Ligand 2 in Regulating the Susceptibility and Chronic Progression of Experimental Autoimmune Encephalomyelitis, The Journal of Immunology, (2006), 176:3480-3489.
Office Action dated Jun. 24, 2014 in U.S. Appl. No. 13/630,364.
Office Action dated Sep. 22, 2014 in U.S. Appl. No. 13/630,364.
Office Action dated Mar. 4, 2015 in U.S. Appl. No. 13/630,364.
Notice of Allowance dated Jun. 12, 2015 in U.S. Appl. No. 13/630,364.

\* cited by examiner

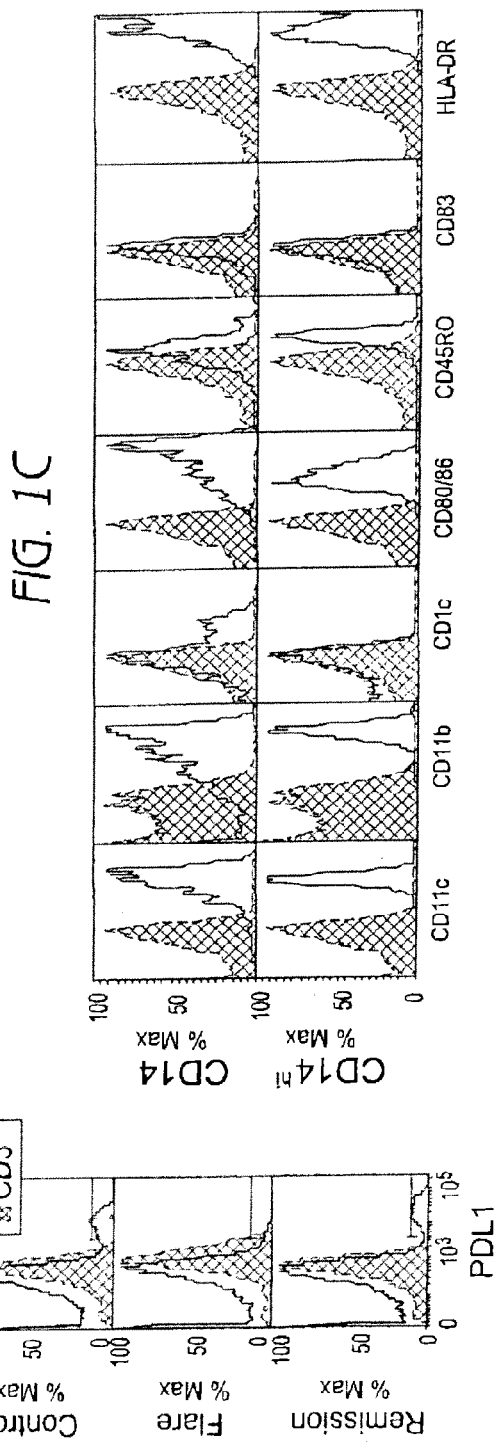
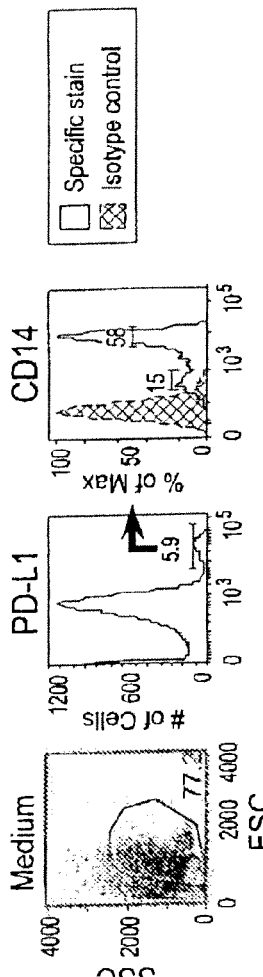
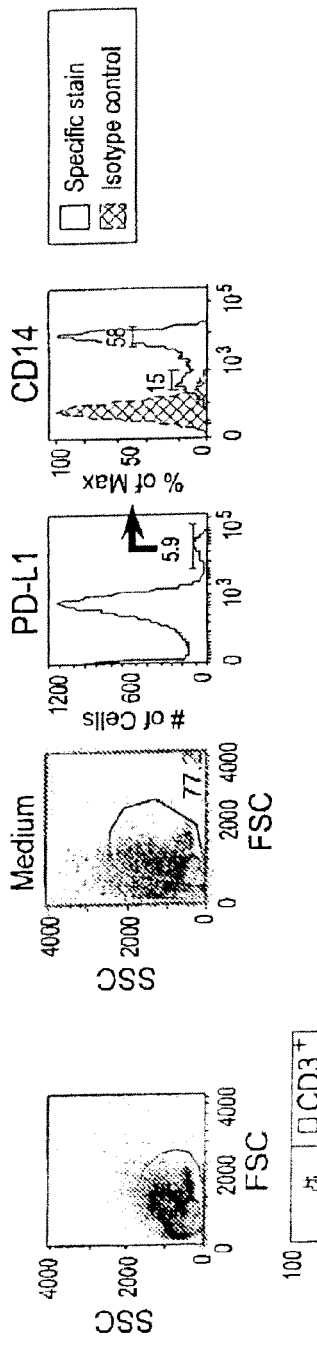

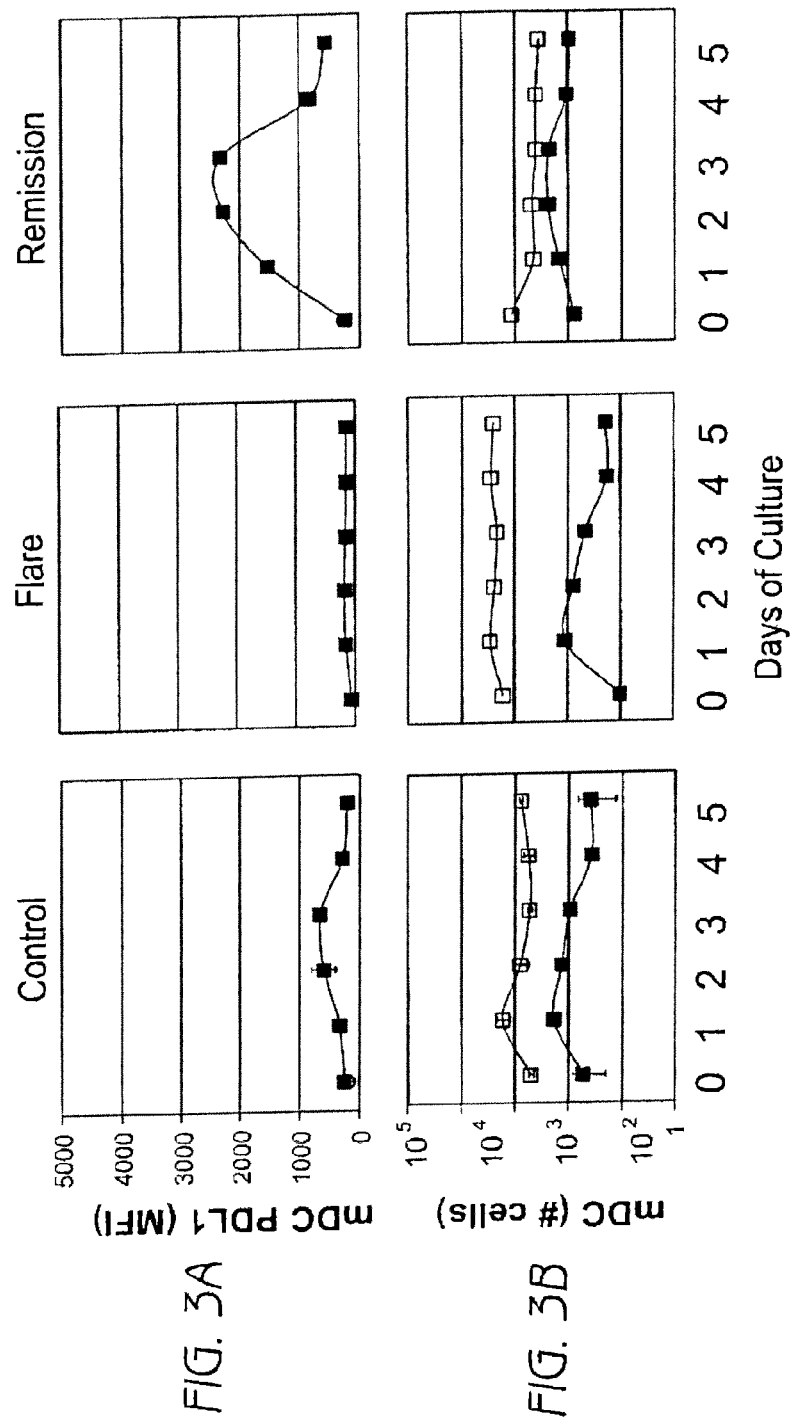

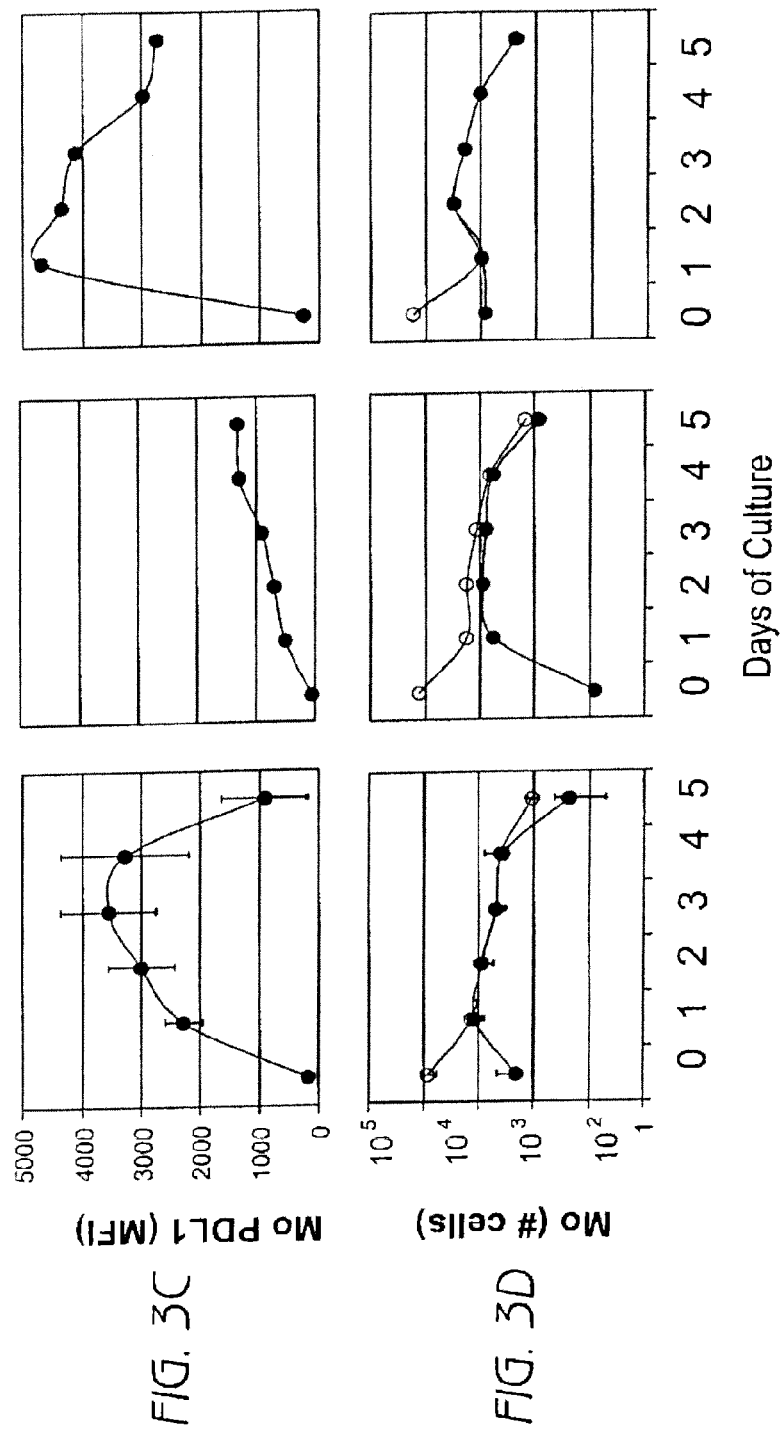

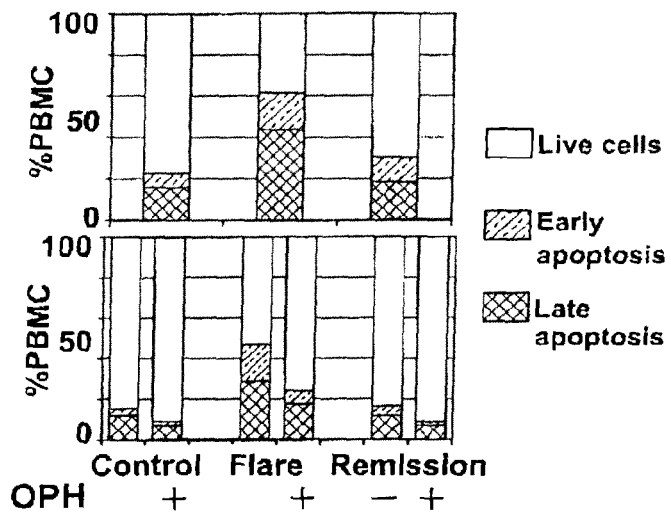
FIG. 4A
FIG. 4B
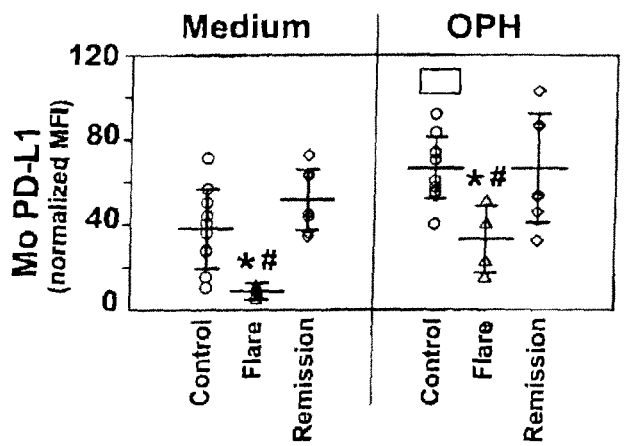
FIG. 4C
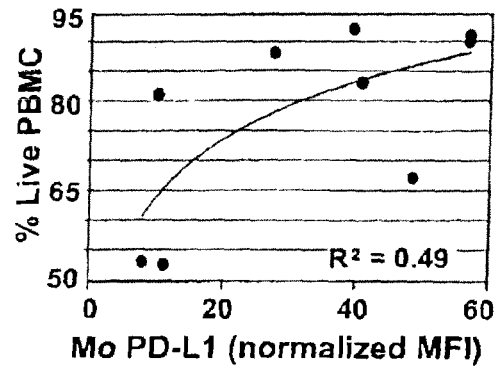
FIG. 4D

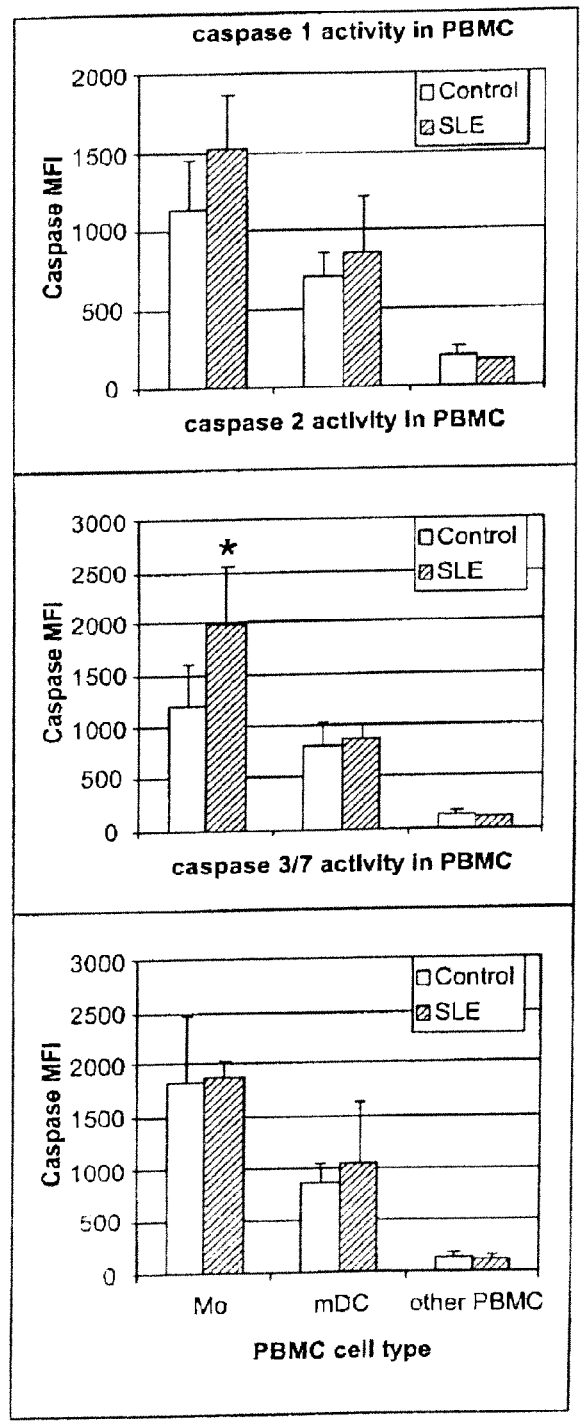
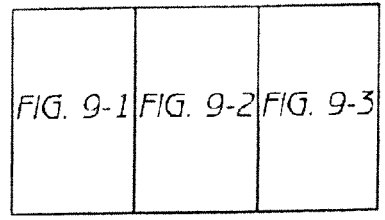
FIG. 9
FIG. 9-1

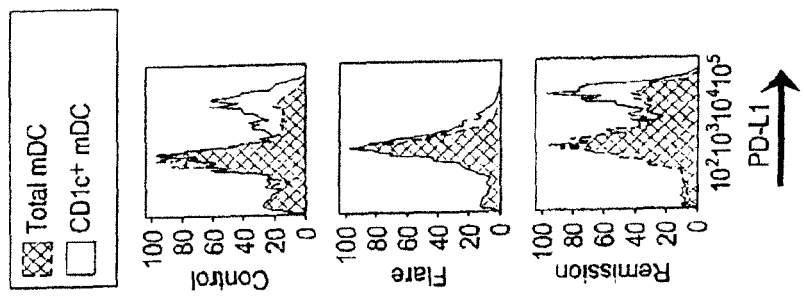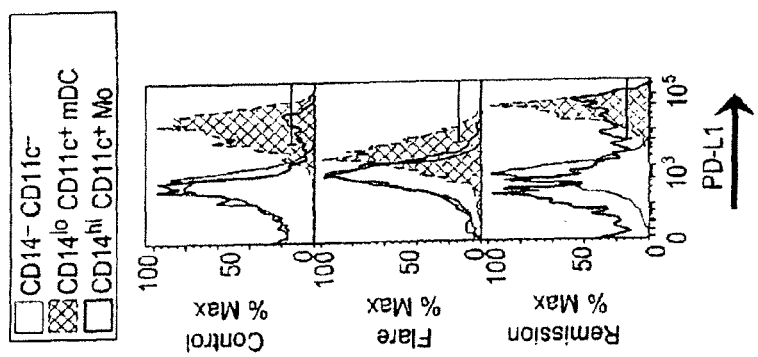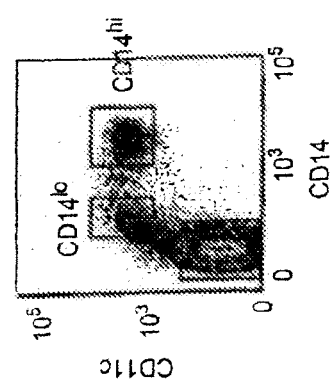

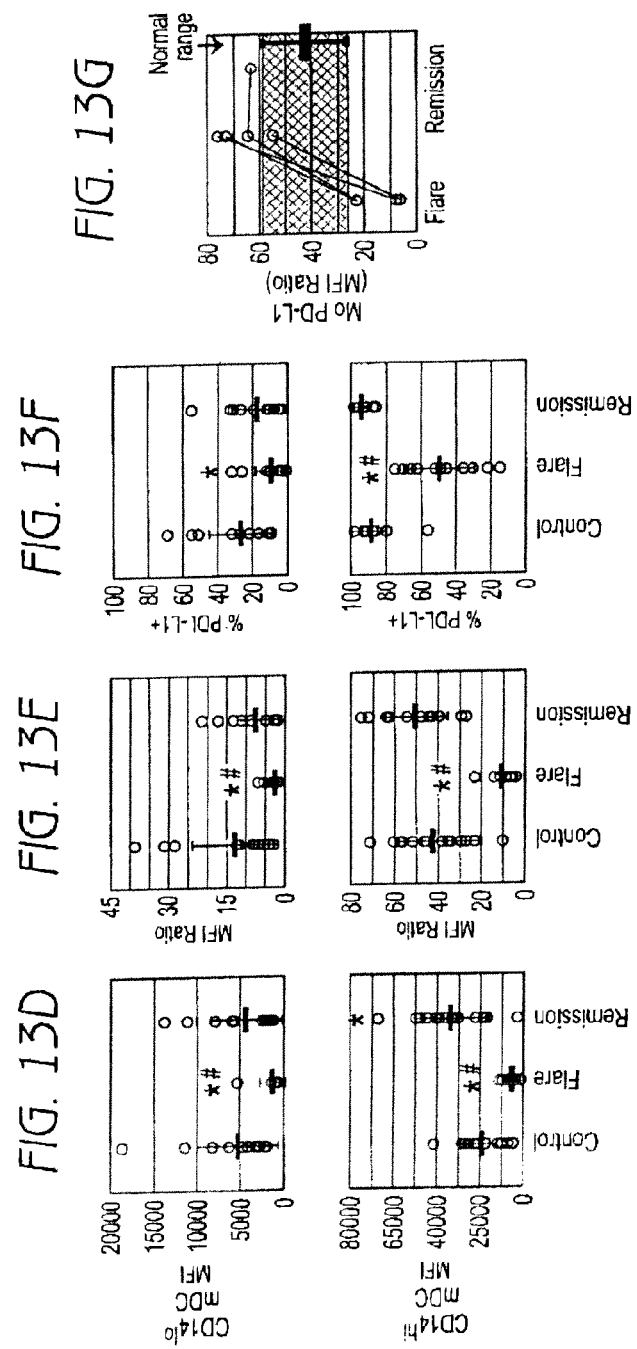

DETECTION AND TREATMENT OF AUTOIMMUNE DISORDERS

CROSS-REFERENCE TO RELATED APPLICATIONS

This application is a continuation of U.S. application Ser. No. 13/630,364, filed on Sep. 28, 2012, now U.S. Pat. No. 9,168,296, which is a continuation of U.S. application Ser. No. 13/282,334, filed Oct. 26, 2011, which is a divisional of U.S. application Ser. No. 12/243,913, filed on Oct. 1, 2008, now U.S. Pat. No. 8,062,852, which claims the benefit of U.S. Provisional Application No. 60/997,334, filed Oct. 1, 2007, all of which are incorporated by reference herein in their entirety.

STATEMENT REGARDING FEDERALLY SPONSORED R&D

This invention was made with Government support under grant T32 AR007108 to the University of Washington Division of Rheumatology from the National Institutes of Health, and grant MOI-RR-00037 to the University of Washington General Clinical Research Center from the National Institutes of Health.

FIELD OF THE INVENTION

Aspects of the invention concern ligands that interact with the inhibitory receptor Programmed death 1 (PD-1), which is expressed on activated lymphocytes and regulates tolerance and autoimmunity. Some embodiments relate to, for example, the use of a PD-1 ligand, such PD-L1, to treat or prevent an autoimmune disease, ameliorate the symptoms of an autoimmune disease or indicate the presence or absence (e.g., diagnose) an autoimmune disease, such as systemic lupus erythematosus (SLE).

BACKGROUND

Autoimmune diseases occur when an organism's immune system fails to recognize some of the organism's own tissues as "self" and attacks them as "foreign." Normally, self-tolerance is developed early by developmental events within the immune system that prevent the organism's own T cells and B cells from reacting with the organism's own tissues. Major histocompatibility complex (MEW) cell surface proteins help regulate these early immune responses by binding to and presenting processed peptides to T cells.

This self-tolerance process breaks-down when autoimmune diseases develop. In such diseases, the organism's own tissues and proteins are recognized as "autoantigens" and are attacked by the organism's immune system. For example, multiple sclerosis is believed to be an autoimmune disease, which occurs when the immune system attacks the myelin sheath, whose function is to insulate and protect nerves. It is a progressive disease characterized by demyelination, followed by neuronal and motor function loss. Rheumatoid arthritis ("RA") is also believed to be an autoimmune disease, which involves chronic inflammation of the synovium in joints with infiltration by activated T cells, macrophages and plasma cells, leading to a progressive destruction of the articular cartilage. It is the most severe form of joint disease. The nature of the autoantigen(s) attacked in rheumatoid arthritis is poorly understood, although collagen type II is a candidate.

Some believe that multiple sclerosis and rheumatoid arthritis are inherited disorders because these diseases occur more frequently in individuals carrying one or more characteristic MHC class II alleles. For example, inherited susceptibility for rheumatoid arthritis is strongly associated with the MEW class II DRB1 *0401, DRB 1 *0404, or DRB 1*0405 or the DRB1*0101 alleles. The human leukocyte antigens (HLA) are found on the surface of cells and help determine the individuality of tissues from different persons. HLA genes are located within the MEW on chromosome 6. The MHC region expresses a number of distinctive classes of molecules in various cells of the body, the genes being, in order of sequence along the chromosome, the Class I, II and III MEW genes. The Class I genes consist of HLA genes, which are further subdivided into A, B and C subregions. The Class II genes are subdivided into the DR, DQ and DP subregions. The MHC-DR molecules are the best known; these occur on the surfaces of antigen presenting cells such as macrophages, dendritic cells of lymphoid tissue and epidermal cells. The Class III MEW products are expressed in various components of the complement system, as well as in some non-immune related cells.

Another example of an autoimmune disease is Systemic lupus erythematosus (SLE), or lupus, which is a debilitating autoimmune disease characterized by the presence of an array of autoantibodies, including antibodies to double stranded DNA, to nuclear protein antigens and to ribonucleoproteins. SLE affects approximately 1 in 2000 individuals (U.S. 1 in 700 women). The disease primarily affects young women, with a female-to male ratio of approximately 9:1.

Systemic lupus can affect almost any organ or system of the body. Systemic lupus may include periods in which few, if any, symptoms are evident ("remission") and other times when the disease becomes more active ("flare"). Most often when people mention "lupus," they are referring to the systemic form of the disease.

Corticosteroids are the mainstay in treating systemic autoimmune disorders. Life threatening, severely disabling manifestations of SLE are treated with high doses of glucocorticoids. Undesirable effects of chronic glucocorticoids include an array of prominent adverse effects such as cushingoid habitus, central obesity, hypertension, infection, capillary fragility, hirsutism, accelerated osteoporosis, cataracts, diabetes mellitus, myopathy and psychosis. In addition to corticosteroid toxicity, patient compliance to a dosage regimen also poses a serious problem.

Cytotoxic agents are also used for controlling active disease, reducing the rate of disease flares, and reducing steroid requirements. Undesirable side effects of the latter include bone marrow suppression, increased infections with opportunistic organisms, irreversible ovarian failure, alopecia and increased risk of malignancy.

Programmed death 1 (PD-1), an inhibitory receptor expressed on activated lymphocytes, is thought to be involved in autoimmune diseases, such as SLE. PD-1 has two ligands: PD-1 ligand 1 (PD-L1), which is expressed broadly on hematopoietic and parenchymal cells, including pancreatic islet cells; and PD-L2, which is restricted to macrophages and dendritic cells.

SLE is an inflammatory disease for which to date there is no definitive diagnostic tool, treatment or cure. The disease results in acute and chronic complications. The only current treatments available are palliative, aimed at relieving acute symptoms and preventing chronic complications, often with profound side effects. The need for new detection methods and treatments for autoimmune diseases, such as SLE are manifest.

SUMMARY OF THE INVENTION

Some embodiments related to method of detecting the presence or absence of an autoimmune disease in a patient comprising:

identifying a patient that is suspected of having or is at risk of having an autoimmune disease;

obtaining a biological sample from said patient;

determining the level of PD-L1 or antibody specific for PD-L1 in said biological sample; and correlating the level of PD-L1 or antibody specific for PD-L1 in said biological sample with the presence or absence of an autoimmune disease.

In some embodiments, the autoimmune disease is selected from the group consisting of multiple sclerosis, Crohn's disease, SLE, Alzheimer's disease, rheumatoid arthritis, psoriatic arthritis, enterogenic spondyloarthropathies, insulin dependent diabetes mellitus, autoimmune hepatitis, thyroiditis, transplant rejection and celiac disease.

In some embodiments, the autoimmune disease is SLE.

In some embodiments, the autoimmune disease is rheumatoid arthritis.

In some embodiments, the biological sample comprises at least one of cells, cell extracts, peripheral blood lymphocytes, serum, plasma and biopsy specimens.

Some embodiments further comprise providing an antibody that is specific for PD-L1.

Some embodiments further comprise providing an antibody specific for a to cell surface marker on a monocyte or dendritic cell.

In some embodiments, the antibody is fluorescently-labeled.

In some embodiments, the determining step employs flow cytometry.

Some embodiments relate to a method of distinguishing between the presence of SLE or a bacterial or viral infection in a patient comprising:

identifying a patient that is suspected of having or is at risk of having an SLE, a bacterial, or viral infection;

obtaining a biological sample from said patient;

determining the level of PD-L1 or antibody specific for PD-L1 in said biological sample; and correlating the presence, absence, or amount of PD-L1 or antibody specific for PD-L1 in said biological sample with the presence or absence of SLE or a bacterial or viral infection.

In some embodiments, the biological sample at least one of cells, cell extracts, peripheral blood lymphocytes, serum, plasma and biopsy specimens Some embodiments further comprise providing an antibody that is specific for PD-L1.

Some embodiments further comprise providing an antibody specific for a to cell surface marker on a monocyte or dendritic cell.

In some embodiments, the antibody is fluorescently-labeled.

In some embodiments, the determining step employs flow cytometry.

Some embodiments relate to a method of distinguishing between an active autoimmune disease and an autoimmune disease in remission in a patient comprising the steps of:

identifying a patient that is suspected of having an active autoimmune disease or an autoimmune disease in remission;

obtaining a biological sample from said patient;

determining the level of PD-L1 or antibody specific for PD-L1 in said biological sample; and correlating the presence, absence, or amount of PD-L1 or antibody specific for PD-L1 in said biological sample with the presence of an active autoimmune disease or an autoimmune disease in remission.

In some embodiments, the autoimmune disease is at least one selected from the group consisting of multiple sclerosis, Crohn's disease, SLE, Alzheimer's disease, rheumatoid arthritis, psoriatic arthritis, enterogenic spondyloarthropathies, insulin dependent diabetes mellitus, autoimmune hepatitis, thyroiditis, transplant rejection and celiac disease.

In some embodiments, the autoimmune disease is SLE.

In some embodiments, the autoimmune disease is rheumatoid arthritis.

In some embodiments, the biological sample comprises at least one of cells, cell extracts, peripheral blood lymphocytes, serum, plasma and biopsy specimens.

Some embodiments further comprise providing an antibody that is specific for PD-L1.

Some embodiments further comprise providing an antibody specific for a cell surface marker on a monocyte or dendritic cell.

In some embodiments, the antibody is fluorescently-labeled.

In some embodiments, the determining step employs flow cytometry.

Some embodiments relate to a kit for detecting the presence of an autoimmune disease comprising:

an antibody specific for PD-L1; and a correlation of the amount of bound antibody specific for PD-L1 or antibody specific for PD-L1 in a biological sample with the presence or absence of said autoimmune disease.

In some embodiments, the autoimmune disease is SLE.

In some embodiments, the autoimmune disease is rheumatoid arthritis.

Some embodiments relate to a method of treating or preventing an autoimmune disease or treating or preventing the symptoms of an autoimmune disease comprising the steps of:

identifying a patient in need of such treatment; and administering to the patient at least one caspase inhibitor in an amount sufficient to induce or increase PD-L expression by the cells of the patient, thereby treating or preventing the autoimmune disease or treating or preventing the symptoms of the autoimmune disease.

In some embodiments, the at least one caspase inhibitor comprises a polycaspase inhibitor.

In some embodiments, the at least one caspase inhibitor comprises at least one of Z-WEHD-fmk, Z-VDVAD-fmk, Z-DEVD-fmk, Z-YVAD-fmk, Z-VEID-fmk, Z-IETD-fmk Z-LEHD-fmk, Z-AEVD-fmk, Z-LEED-fmk, Z-VAD-fmk and OPH.

In some embodiments, the capase inhibitor is OPH.

In some embodiments, the autoimmune disease is SLE.

In some embodiments, the autoimmune disease is rheumatoid arthritis.

In some embodiments, the administering of the caspase inhibitor to the patient comprises at least one of intravenous, intraperitoneal, inhalation, intramuscular, subcutaneous, nasal and oral administration.

Some embodiments further comprise the administration of at least one selected from therapeutics targeting HLA molecules, CD18, CD2, CD4, CD28, Fc-gamma 3 receptor, Fc gamma receptor 2a, CTLA4, or TGF-b in an amount sufficient to induce or increase PD-L1 expression by the cells of the patient.

Some embodiments relate to a method of treating or preventing an autoimmune disease or treating or preventing the symptoms of an autoimmune disease comprising the steps of:
 identifying a patient in need of such treatment;
 removing a biological sample from the patient;
 exposing the biological sample to at least one caspase inhibitor ex vivo in an amount sufficient to induce or increase the expression of PD-L1 on the cells in the biological sample;
 washing the cells; and
 administering the cells to the patient thereby treating or preventing the autoimmune disease or treating or preventing the symptoms of the autoimmune disease.

In some embodiments, the at least one caspase inhibitor comprises a poly caspase inhibitor.

In some embodiments, the biological sample comprises at least one of cells, cell extracts, peripheral blood lymphocytes, serum, plasma and biopsy specimens.

In some embodiments, the at least one caspase inhibitor comprises at least one of Z-WEHD-fmk, Z-VDVAD-fmk, Z-DEVD-fmk, Z-YVAD-fmk, Z-VEID-fmk, Z-IETD-fmk Z-LEHD-fmk, Z-AEVD-fmk, Z-LEED-fmk, Z-VAD-fmk and OPH.

In some embodiments, the caspase inhibitor is OPH.

In some embodiments, the autoimmune disease is SLE.

In some embodiments, the autoimmune disease is rheumatoid arthritis.

Some embodiments further comprise the step of exposing biological sample to at least one selected from therapeutics targeting HLA molecules, CD18, CD2, CD4, CD28, Fc-gamma 3 receptor, Fc gamma receptor 2a, CTLA4, or TGF-b in an amount sufficient to induce or increase PD-L1 expression by the cells of the patient.

BRIEF DESCRIPTION OF THE DRAWINGS

FIGS. 1A-1C show the PD-L1 expression in primary human PBMC. Cells were cultured for one day and live PBMC gated by forward and side scatter. FIG. 1A, PD-L1 is expressed by the CD3$^-$ population in controls and in SLE remission, but not in SLE flare. FIG. 1B, PD-L1$^+$ cells could be divided into 2 groups based on CD14 expression. For FIGS. 1A and 1B, results are representative of PBMC from 17 healthy controls, 12 SLE flare, and 12 SLE remission. FIG. 1C, CD14$^{lo}$ and CD14$^{hi}$ cells were further characterized using antibodies to CD11c, CD11b, CD1c, CD80/CD86, CD45RO, CD83, and HLA-DR. Results are representative of PBMC from 2 controls, 1 SLE flare, and 1 SLE remission.

FIG. 2A, PD-L1 is expressed on immature mDC and Mo from healthy children and those in SLE remission, but not from those in SLE flare. Data are representative of PBMC from 17 healthy controls, 12 SLE flare, and 12 SLE remission. FIG. 2B, Mean PD-L1 expression is significantly lower on immature mDC and Mo in active SLE. FIG. 2C, PD-L1 expression correlates with SLE disease activity in individual patients. MFI values were normalized using PD-L1 expression on CD14$^-$/CD11c$^-$ cells for each sample. FIG. 2D, Percent of PD-L1$^+$ APC is decreased in active SLE. For FIGS. 2B and 2D: horizontal bars represent means for 15 controls, 12 SLE flare, and 11 SLE remission; C=Controls, F=SLE flare, R=SLE remission.

FIGS. 3A-3D show spontaneous PD-L1 expression in APC over time. PBMC from two healthy controls (means+/− standard deviations), one SLE flare, and one SLE remission were cultured for five days and APC identified by surface staining. FIG. 3A, Immature mDC from children with active SLE fail to upregulate PD-L1 on all days. FIG. 3B, Absolute number of immature mDC (open symbols), and number expressing PD-L1 (filled symbols). FIG. 3C, Mo from children with active SLE fail to upregulate PD-L1; although levels appear to rise slightly by day five, there are very low cell numbers remaining in these cultures (see FIG. 3D). FIG. 3D, Absolute number of Mo (open symbols), and number expressing PD-L1 (filled symbols). Timecourse is representative of three independent experiments with similar results, using PBMC from six healthy controls, six SLE flare, and 11 SLE remission.

FIGS. 4A-4D show that PD-L1 expression is inversely correlated with apoptosis and is upregulated by caspase inhibitors. FIG. 4A, Increased apoptosis in active SLE. PBMC were cultured for one day and stained to identify early (Annexin V$^+$/PI$^-$) and late (Annexin V$^+$/PI$^-$) apoptosis. Data shown represent means for PBMC from six controls, six SLE flare, and ten SLE remission. FIG. 4B, OPH reduces apoptosis in PBMC. Data shown represent means for PBMC from two controls, two SLE flare, and one SLE remission. FIG. 4C. OPH treatment significantly increases PD-L1 expression over baseline. Horizontal bars represent mean Mo PD-L1 levels in ten controls, four SLE flare, and seven SLE remission samples; values were normalized as in 2C. FIG. 4D, Apoptosis is inversely correlated with PD-L1. Percent live PBMC was plotted against Mo PD-L1 expression. Data shown are representative of two independent experiments.

FIG. 5A, OPH increases PD-L1 and increases the number of CD14$^{int}$ among PD-L1$^+$ PBMC. FIG. 5B, OPH does not increase other APC surface markers. Data shown are representative of PBMC from two healthy controls, one SLE flare, and one SLE remission. FIG. 5C, APC express very little PD-L2 after one day of culture. Data are representative of PBMC from three controls and one SLE remission. FIG. 5D, PD-L2 expression is associated with CD14 levels, but is not increased by OPH, Z-VAD, or DMSO control through four days of culture. Bars represent means+/−standard deviations of PD-L2 expression in two healthy controls.

FIGS. 9-1, 9-2, and 9-3 show the levels of caspase activity in PBMC from children with and without SLE. Symbols denote differences between populations: ** p<0.05, demonstrating a significant difference between SLE and controls; *p<0.071, demonstrating a trend toward significance between SLE and controls.

FIGS. 13A-13G show PD-L1 protein is deficient on APC during SLE flare, but not during remission. (FIG. 13A) PBMC were cultured for 1 day and APC subsets identified. (FIG. 13B) PD-L1 expression on both mDC and Mo was reduced during SLE flare, but not during remission. (FIG. 13C) CD1c staining demonstrated that PD-L1 expression in $CD14^{lo}$ $CD11c^{+}$ cells was enriched on Type 1 immature mDC. (FIG. 13D) PD-L1 levels on mDC (upper graph) and Mo (lower graph) from 15 controls, 12 SLE flare and 14 SLE remission. Circles represent individual PD-L1 values and bars represent the mean MFI (±1 s.d.) for each group. For SLE flare mDC, $*P<6.5\times10^{-3}$ compared with controls; $*P<2.5\times10^{-2}$ compared with remission. For SLE flare Mo, $*P<1.8\times10^{-4}$ compared with controls; $*P<2.4\times10^{-6}$ compared with remission. For SLE remission Mo, $*P<3.4\times10^{-3}$ compared with controls. (FIG. 13E) PD-L1 expression on mDC and Mo was normalized to background levels using the PD-L1 MFI of CD $14^{-}$ $CD11c^{-}$ cells as the denominator for each sample. For SLE flare mDC, $*P<4.1\times10^{-3}$ compared with controls; $*P<2.1\times10^{-2}$ compared with remission. For SLE flare Mo, $*P<2.0\times10^{-8}$ compared with controls; $*P<1.1\times10^{-8}$ compared with remission. (FIG. 13F) SLE flare patients exhibited a lower percentage of $PD-L1^{-}$ APC (mDC, upper graph and Mo, lower graph). For SLE flare mDC, $*P<4.2\times10^{-3}$ compared with controls. For SLE flare Mo, $*P<1.1\times10^{-6}$ compared with controls; $*P<4.0\times10^{-8}$ compared with remission. FIG. 13G Mo PD-L1 values from (FIG. 13E) were graphed for patients with serial blood samples; shaded area denoted the 'normal range' of Mo PD-L1 expression observed in healthy controls (mean±1 s.d.).

DETAILED DESCRIPTION OF THE INVENTION

Figure 2A:
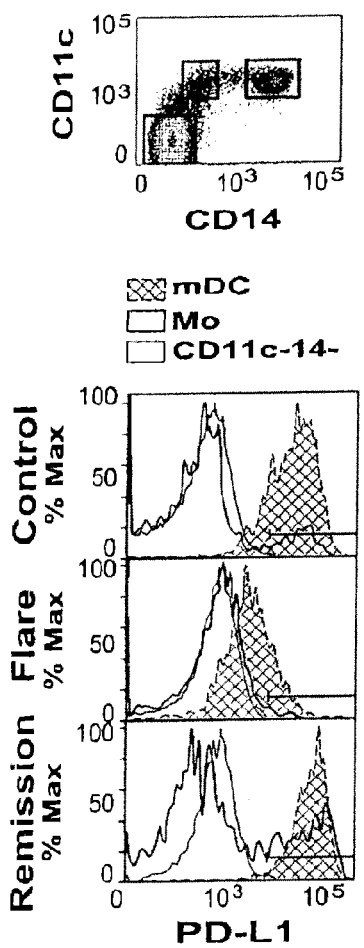
FIGS. 2A-2D show APC from subjects with active SLE are deficient in PD-L1.

Several embodiments described herein are related to the identification, amelioration, and/or treatment of a wide variety of autoimmune or immune related diseases or disorders including, for example, multiple sclerosis, Crohn's disease, SLE, Alzheimer's disease, rheumatoid arthritis, psoriatic arthritis, enterogenic spondyloarthropathies, insulin dependent diabetes mellitus, autoimmune hepatitis, thyroiditis, transplant rejection and celiac disease.

Some embodiments concern the use of a PD-L1 leukocyte expression assay to identify the presence, absence, or progression of an autoimmune disease, for example. More embodiments relate to the use of a PD-L1 agonist or ligand to ameliorate or treat an autoimmune disease. Some embodiments concern methods, wherein a PD-L1 ligand is provided to a patient that has been identified as having an autoimmune disease, such as SLE, and the general health or welfare of the patient is improved during the course of treatment. Optionally, the improvement in said patient is monitored or measured before, during, or after administration of said PD-L1 ligand using conventional clinical evaluation or observation, analysis of diagnostic markers for the disease, or by using one or more of the diagnostic techniques described herein.

Active SLE is associated with failure of antigen presenting cells to upregulate programmed cell death ligand-1. Antigen presenting cells (APC) maintain peripheral T cell tolerance in part via expression of negative costimulatory molecules such as programmed cell death ligand-1 (PD-L1). APC in peripheral blood, including CD14+/CD11c+ monocytes (Mo) and CD14−/CD11c+ myeloid dendritic cells (mDC), have been implicated in the pathogenesis of SLE. Patients with active disease generally have decreased numbers of Mo in peripheral blood mononuclear cells, and their APC generally fails to upregulate PD-L1 appropriately when cultured ex vivo, as measured by flow cytometry. APC from healthy individuals or SLE patients in remission tend to upregulate PD-L1 surface expression by day one, with peak expression on day two or three, and declining expression through day six, all in the absence of exogenously-added stimuli. Therefore, failure of APC to upregulate PD-L1 correlates with abnormal T lymphocyte regulation and loss of peripheral tolerance in SLE.

Programmed death ligand-1 (PD-L1; also known as B7-H1/CD274), is a B7 family glycoprotein inducibly expressed on many hematopoietic and parenchymal cells in response to inflammatory stimuli. It regulates immune tolerance by binding to the programmed death-1 (PD-1) receptor on lymphocytes, causing suppression of T-effector function, and permissiveness of regulatory T-cell function. PD-L1 may also suppress T-cell activation by signaling through the B7-1 receptor. Although mRNA for PD-L1 can be found in many healthy human tissues, baseline protein expression appears to be limited to cells of monocytic origin. Both myeloid dendritic cells (mDC) and monocytes (Mo) express PD-L1 protein, and anti-PD-L1 antibody increases the stimulatory capacity of mature and immature DCs for T-effector cells. Endogenous or transgene-driven expression of PD-L1 on antigenpresenting DCs leads to diminished T-cell reactivity in vitro and in vivo, as demonstrated in murine models of autoimmunity. The importance of PD-L1 in self-tolerance has also been demonstrated in experimental animals in which blockade or absence of the PD-L1:PD-1 pathway results in various forms of autoimmune disease, including a spontaneous lupus-like glomerulonephritis in C57BL/6 mice.

The receptor for PD-L1 is shared by a second ligand, PD-L2, (B7-DC/CD273), which can also inhibit T-cell activation, but is less widely expressed and appears to play some non-redundant roles in self-tolerance. DNA polymorphisms in the gene for the shared PD-1 receptor have been linked to SLE susceptibility in some populations of adults and children; however, T-cell expression of PD-1 protein has not been found to differ significantly between SLE patients and controls. In contrast to the PD-1 gene studies, genetic polymorphisms in PD-L1 did not appear to be linked to SLE. However, both immature mDC and Mo from children with SLE failed to up-regulate PD-L1 normally, and this deficiency was associated with increased disease activity, indicating an important role for this negative co-stimulator in the pathogenesis of SLE.

As discussed above, PD-L1 on antigen presenting cells binds to PD-1 on T lymphocytes, and regulates their activity. Animals without PD-1 develop an autoimmune disease similar to SLE, with T lymphocytes reacting to self proteins. Some embodiments relate to the discovery that patients with active SLE express almost no PD-L1 on their antigen presenting cells. The same patients, when their disease is in remission, express PD-L1.

Accordingly, some embodiments concern methods to identify the presence, absence, or progression of an autoimmune disease, such as SLE, in a subject that has been identified as having an autoimmune disease or a subject identified as being at risk for developing an autoimmune disease, wherein the presence, absence, or amount of PD-L1 in a biological sample from said subject is analyzed, detected, or determined. In some embodiments, such assays are performed by staining peripheral blood lymphocytes obtained from a subject with a fluorescence-labeled antibody specific for PD-L1, along with antibodies to cell surface markers for monocytes and dendritic cells (CD11c and CD14). Optionally, the frequency of cells expressing PD-L1 or the amount of PD-L1 on a subject's peripheral blood lymphocytes in the sample is detected using flow cytometry, ELISA, or other immunological detection techniques. Thus, some embodiments include methods to identify the presence, absence, or likelihood to acquire an autoimmune disease, such as SLE, wherein a molecule that specifically binds to PD-L1, such as an antibody, binding partner for PD-L1, or a binding fragment thereof (e.g., an identifiable ligand for PD-L1), is contacted with a biological sample obtained from a patient (e.g., blood) or a component isolated therefrom (e.g., a peripheral blood lymphocytes) for a time sufficient to create a PD-L1/binding partner complex and the presence, absence, or amount of said PD-L1/antibody or binding partner complex is measured or detected, which then indicates the presence, absence, or likelihood to acquire the autoimmune disease. The assays described above may be used to assess the efficacy of a treatment regimen or the progression of a treatment protocol or the progression of an autoimmune disease. Other embodiments relate to methods to identify individuals that are at risk for developing an autoimmune disease, or individuals that are at risk for relapse of a preexisting autoimmune disease.

The identifiable ligand for PD-L1 or PD-L1 binding partner may be an antibody (e.g., a monoclonal antibody or a polyclonal antibody, which may be humanized or modified) or a fragment of an antibody that binds to a PD-L1 antigen. Polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988). Antigen-binding fragments of such antibodies, which may be produced using conventional techniques, are also encompassed by the present invention. Examples of such fragments include, but are not limited to, Fab, F(ab'), and F(ab')$_2$ fragments. Antibody fragments and derivatives produced by genetic engineering techniques are also provided. The monoclonal antibodies may be chimeric antibodies, e.g., humanized versions of murine monoclonal antibodies. Such humanized antibodies may be prepared by known techniques. In some embodiments, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993).

The identifiable PD-L1 ligand or binding partner for PD-L1 may also be a peptide or peptidomimetic that binds to PD-L1. Peptides and peptidomimetics that bind to PD-L1 can be identified using computer modeling of the binding regions of antibodies that interact with PD-L1 and identifying peptides and peptidomimetics with similar structures. Peptides and peptidomimetics that bind to PD-L1 can also be identified by screening detectably labeled PD-L1 against libraries of peptides and peptidomimetics and determining the presence of detectably labeled PD-L1/binding partner complexes. Alternatively, detectably labeled peptides and peptidomimetics can be screened against PD-L1 and the presence of detectably labled binding partner/PD-L1 complexes can be identified. Preferably, the ligands for PD-L1 (e.g., an antibody, a PD-L1 antigen-binding fragment thereof or PD-L1 ligand) is detectably labeled. The label may be colorimetric, fluorescent, a radioisotope, or a metal.

More embodiments relate to the use of PD-L1 or a nucleic acid encoding PD-L1 as a therapeutic to regulate T lymphocytes in patients suffering from an autoimmune disease, such as SLE. In some embodiments, for example, PD-L1 is provided to or administered to a patient that has been identified as having an autoimmune disease, such as SLE, and the presence, absence, or progression of the autoimmune disease or a marker thereof is measured or detected using clinical evaluation or diagnostic assay. In more embodiments, a nucleic acid encoding PD-L1 (e.g., DNA or RNA), preferably a nucleic acid that has been codon optimized for expression in humans is provided or administered to a patient that has been identified as having an autoimmune disease, such as SLE, and the presence, absence, or progression of the autoimmune disease or a marker thereof is measured or detected using clinical evaluation or diagnostic assay.

Some additional embodiments relate to methods of inducing or increasing PD-L1 expression in patients. In some embodiments, for example, caspase inhibitors can be administered to a patient with autoimmune disease in order to induce or increase PD-L1 expression in the patient, thereby treating or preventing the autoimmune disease or ameliorating the symptoms of the autoimmune disease. Such inducement or increase can be achieved by administering to the patient an amount of at least one caspase inhibitor in an amount sufficient to induce or cause an increase in the expression of PD-L1 by a patient's cells. In some embodiments, the caspase inhibitors can be combined with one or more therapeutic capable of treating or preventing the autoimmune disease or ameliorating the symptoms of the autoimmune disease. In certain embodiments, the caspase inhibitors can be specific caspase inhibitors, pan caspase inhibitors, poly-caspase inhibitors or a combination thereof. In some embodiments, the caspase inhibitors are, for example, at least one of Z-WEHD-fmk, Z-VDVAD-fmk, Z-DEVD-fmk, Z-YVAD-fmk, Z-VEID-fmk, Z-IETD-fmk Z-LEHD-fmk, Z-AEVD-fmk, Z-LEED-fmk, Z-VAD-fmk and OPH. However, the current embodiments are not limited to such examples and encompass any pharmaceutically acceptable caspase inhibitor.

More embodiments relate to methods of inducing or increasing PD-L1 expression by the cells of a patient by removing cells from the patient and exposing the cells to at least one caspase inhibitor ex vivo in order to induce or increase the expression of PD-L1 on the cells, washing the cells and then administering the cells to a patient.

In some embodiments, an additional therapeutic can be combined with at least one caspase inhibitor that is either administered to the patient in vivo or exposed to cells of the patient ex vivo to induce or increase PD-L1 expression by the cells. Examples of such additional therapeutics include therapeutics targeting HLA molecules, CD18, CD2, CD4, CD28, Fc-gamma 3 receptor, Fc gamma receptor 2a, CTLA4, or TGF-b.

Example 1

PD-L1 Protein Levels Downmodulated in Control Mo Using Specific siRNA

In this model, siRNA technology was used to diminish mRNA for PD-LI. Normal PBMC were obtained from healthy volunteers and frozen in liquid nitrogen. At the time of experiments, cells were thawed, washed, and diluted to $1-2 \times 10^6$ cells/ml in culture medium consisting of RPMI 1640 supplemented with L-glutamine (CellGro), 10% heat-inactivated AB human serum, 1% penicillin/streptomycin (CellGro), and 0.1% beta-mercaptoethanol. Cells were plated in round-bottom 96-well plates (Corning Costar) and incubated at 37° C. in a humidified cell chamber with 5% $CO_2$. After a four-hour rest period, total PBMC were incubated with Mo nucleofection buffer (Amaxa) plus specific anti-human PD-L1 siRNA or control siRNA (sc-39699, Santa Cruz Biotechnology, Inc.) and nucleofected as per the manufacturer's protocol (Amaxa).

PBMC were returned to the incubator and cell surface PD-L1 levels determined by flow cytometry 24 hours later. Cells were surface-stained using various fluorochrome- or biotin-conjugated monoclonal antibodies, including: anti-CD3, anti-PD-L1 (eBioscience), anti-CD11c, and anti-CD14, (Pharmingen/BD Biosciences), with isotype-matched, fluorochrome-/biotin-labeled irrelevant monoclonal antibodies as controls. Some cells were cultured for longer time periods to assay the level of intracellular proteins (cytokines and Foxp3). To determine intracellular caspase activity, selected cultures were incubated with a cell-permeant fluorochrome-derivative of the appropriate caspase inhibitor for each caspase under investigation.

Prior to staining for intracellular cytokines, cells were restimulated for four hours with 1 ug/ml phorbol myristate acetate (PMA) plus 14 uM ionomycin, in the presence of GolgiStop (BD Biosciences) to prevent cytokine secretion. Cells were permeabilized with the appropriate proprietary buffers according to the manufacturer's protocols (BD Biosciences, eBioscience, or BioLegend), and intracellular cytokine production was assayed using fluorochrome-conjugated monoclonal antibodies to interferon-gamma (IFN-$\gamma$), tumor necrosis factor-alpha (TNF-$\alpha$), and interleukin-17 (IL-17) (Pharmingen/BD Biosciences). Prior to staining for Foxp3 (BioLegend), cells were permeabilized, but not restimulated. All samples were blocked using 0.5% human serum and anti-FcR antibody (Miltenyi) during staining. Dead cells were excluded from the analysis using a dead cell marker dye. After staining, PBMC were fixed using 2% paraformaldehyde in PBS after preliminary experiments indicated no effect of cell fixation on expression levels of PD-L1 or other surface markers. Flow cytometry was performed using an LSR II cytometer (Becton Dickinson), and the data were analyzed using FlowJo software (Macintosh Version 6.3). Mo and immature myeloid DC (mDC) were identified using surface markers characteristic of each cell type. Results were compared between populations using Student's t-test, and significance assigned where $p<0.05$.

In the siRNA studies it was confirmed that the distribution of leukocyte subtypes in PBMC were not altered by this experimental manipulation (Table I), and that the number of cells expressing PD-L1 also remained unchanged in these cultures (Table II). However, expression of PD-L1 protein on Mo and mDC was reduced by 24 hours (Table III), while the levels PD-L1 of on other PBMC subsets remained unchanged.

TABLE I

Leukocyte subsets in nucleofected PBMC from two healthy controls.

| | Ancestry Subset Value Type For | | | | |
|---|---|---|---|---|---|
| | % Live of Lymphs | % CD14+ of Live | % CD1c+ of Live | % CD11c+ of Live | % CD3+ of Live |
| Mbr No Stain Control | 99 | 0 | 0.02 | 0.03 | 0 |
| Mbr IgG Control Control | 90 | 1.3 | 3.9 | 29 | 58 |
| NOP511(2) d1 PDL1 High Control siRNA | 73 | 4.2 | 2.7 | 25 | 52 |
| NOP511(2) d1 PDL1 Low PDL1 siRNA | 76 | 5.4 | 3.2 | 29 | 54 |

TABLE I-continued

Leukocyte subsets in nucleofected PBMC from two healthy controls.

| | Ancestry Subset Value Type For | | | | |
|---|---|---|---|---|---|
| | % Live of Lymphs | % CD14+ of Live | % CD1c+ of Live | % CD11c+ of Live | % CD3+ of Live |
| NOP511(2) d1 PDL1 High PDL1 siRNA | 74 | 5.5 | 3.5 | 33 | 54 |
| NOP505A(2) d1 PDL1 High Control siRNA | 66 | 1.3 | 2.3 | 27 | 59 |
| NOP505A(2) d1 PDL1 Low PDL1 siRNA | 69 | 2.3 | 3.3 | 27 | 56 |
| NOP505A(2) d1 PDL1 High PDL1 siRNA | 63 | 1.3 | 3.4 | 29 | 56 |
| NOP505A(2) d1 PDL1 GFP vector no zap | 75 | 2.5 | 2.7 | 27 | 57 |

PBMC from two healthy individuals were subjected to nucleofection using control siRNA or two different concentrations of PD-L1 siRNA and results compared with those in nonnucleofected control cultures to confirm that specific leukocyte subsets were not remaining in culture at the end of day one.

TABLE II

Percent of each leukocyte subset expressing PD-L1 after nucleofection.

| | Ancestry Subset Value Type For | | | | |
|---|---|---|---|---|---|
| | % PDL1+ of Live | % PDL1+ of CD14+ | % PDL1+ of CD1c+ | % PDL1+ of CD11c+ | % PDL1+ of CD3+ |
| Mbr No Stain Control | 0 | * | 0 | 0 | * |
| Mbr IgG Control Control | 0.8 | 0.4 | 1.7 | 26 | 0.8 |
| NOP511(2) d1 PDL1 High Control siRNA | 7.2 | 97 | 8.7 | 15 | 4 |
| NOP511(2) d1 PDL1 Low PDL1 siRNA | 6.7 | 91 | 7.5 | 16 | 2.1 |
| NOP511(2) d1 PDL1 High PDL1 siRNA | 7.2 | 91 | 7.8 | 17 | 2.7 |
| NOP505A(2) d1 PDL1 High Control siRNA | 3.2 | 75 | 7.6 | 7.3 | 2.2 |
| NOP505A(2) d1 PDL1 Low PDL1 siRNA | 3.7 | 64 | 2.7 | 8.9 | 2.4 |
| NOP505A(2) d1 PDL1 High PDL1 siRNA | 5.1 | 67 | 7.2 | 11 | 4.6 |
| NOP505A(2) d1 PDL1 GFP vector no zap | 3 | 61 | 9 | 8.1 | 1.9 |

PBMC from two healthy individuals were subjected to nucleofection using control siRNA or two different concentrations of PD-L1 siRNA and results compared with those in nonnucleofected control cultures to confirm that the percent of cells in each specific leukocyte subset was not altered by this manipulation. Numbers represent percent of each cell type expressing PD-L1 in culture at the end of day one.

TABLE III

PD-L1 expression in nucleofected leukocyte subsets.

| | Ancestry Subset Value Type For | | | |
|---|---|---|---|---|
| | PDL % MFI of CD14+ | PDL1 MFI of CD1c+ | PDL1 MFI of CD11c+ | PDL1 MFI of CD3+ |
| Mbr No Stain Control | * | 298 | 113 | * |
| Mbr IgG Control Control | 151 | 240 | 325 | 172 |
| NOP511(2) d1 PDL1 High Control siRNA | 13578 | 775 | 2398 | 557 |
| NOP511(2) d1 PDL1 Low PDL1 siRNA | 7699 | 621 | 1741 | 410 |
| NOP511(2) d1 PDL1 High PDL1 siRNA | 7013 | 690 | 1608 | 299 |
| NOP505A(2) d1 PDL1 High Control siRNA | 5405 | 635 | 864 | 322 |
| NOP505A(2) d1 PDL1 Low PDL1 siRNA | 3108 | 255 | 599 | 332 |
| NOP505A(2) d1 PDL1 High PDL1 siRNA | 3512 | 420 | 675 | 434 |
| NOP505A(2) d1 PDL1 GFP vector no zap | 3582 | 535 | 640 | 308 |

PBMC from two healthy individuals were subjected to nucleofection using control siRNA or two different concentrations of PD-L1 siRNA and results were compared with those in nonnucleofected control cultures to confirm that PD-L1 was specifically downmodulated in CD14+ Mo and mDC, while other cell types were unaffected. Numbers represent mean fluorescence intensity (MFI) of PD-L1 in of each cell type under various treatment conditions at the end of day one. Symbols represent **$p<5\times10^{-5}$, #$p<0.033$, and *$p<5\times10^{-4}$.

In order to allow interaction of APC with autologous T cells, a culture of each PBMC sample was incubated for another four days. At the end of this time, PBMC were assessed for intracellular cytokine production in T lymphocytes as well as for expression levels of the regulatory T cell marker, Foxp3. Although Mo treated with siRNA expressed significantly lower amounts of surface PD-L1, production of IFN-γ, TNF-α, and IL-17, and the level of intracellular Foxp3 expression remained unchanged in T cells. The T cells examined in these studies were autologous cells, incubated and treated concurrently with the APC, thus (1) limiting the number and magnitude of the T lymphocyte response as compared to an allogeneic reaction, and (2) allowing the possibility that T cells in these cultures may have been affected by the nucleofection process itself, even though preliminary studies gave no indication of adverse effects on T cell survival or function. These experiments showed that the distribution of leukocyte subtypes in PBMC were not altered by this experimental manipulation (Table I), and that the number of cells expressing PD-L1 also remained unchanged in these cultures (Table II). Neither of these parameters was altered, however, expression of PD-L1 protein on Mo and mDC were reduced by 24 hours (Table III and FIG. 1), while the levels PD-L1 of on other PBMC subsets remained unchanged.

Example 2

PD-L1 Protein Levels were Increased in APC by Inhibition of Caspase Activity

PBMC were cultured as above and a duplicate well of each sample treated with 50 uM OPH. PD-L1 upregulation on APC was confirmed in these cultures, and an aliquot of each sample was incubated further in order to allow interaction of APC with autologous T cells in culture. Three days later, the cells were fixed and permeabilized, and the T lymphocytes were assayed for intracellular expression of the regulatory T cell protein, Foxp3.

It was found that OPH increased PD-L1 expression on the surface of both Mo and mDC at day one. Identification of endogenous Treg in the PBMC cultures using Foxp3 protein revealed not only fewer Treg in lupus PBMC, but also less Foxp3 protein per cell, indicating that development and/or survival of Treg was abnormal in SLE. Although cultures treated with OPH expressed significantly higher amounts of PD-L1 on the surface of APC, the level of Foxp3 expression in both healthy control and SLE cultures remained unchanged, both with respect to Foxp3 MFI and to the number of CD4+ cells expressing Foxp3. These experiments showed that diminished PD-L1 levels on lupus APC directly affect Treg development.

Example 3

PD-L1 Signaling was Inhibited Using Anti-PD-1 Antibodies

Figure 8:
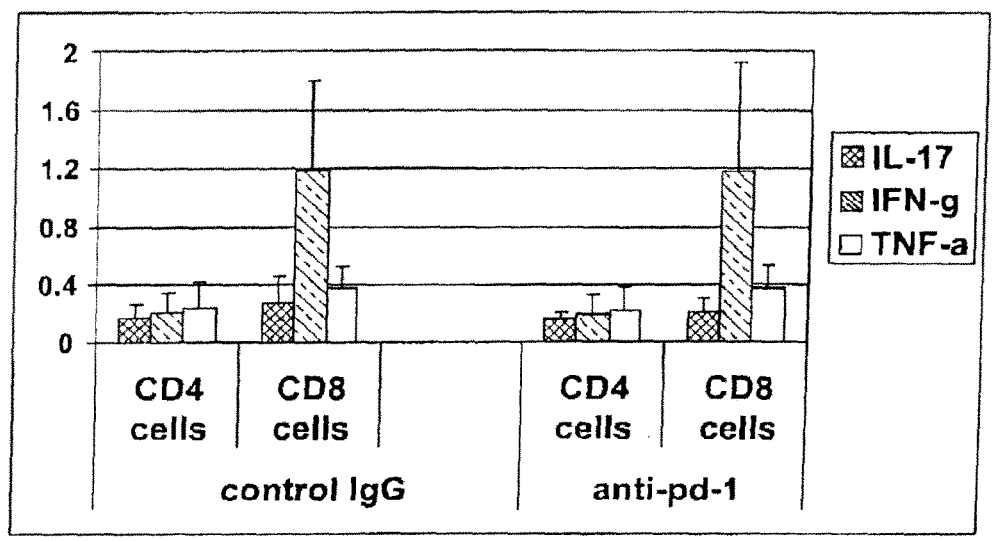
FIG. 8 shows the cytokine expression by T cells in autologous culture. Bars represent the percent of each cell type expressing cytokines (mean+/−S.E.).

Soluble anti-PD-1 antibody was utilized to block PD-L1 signaling in autologous PBMC cultures, and the effect on T cell cytokine production was evaluated after five days of incubation. It was found that soluble anti-PD-1 antibody at this concentration did not significantly affect intracellular production of IFN-γ, TNF-α, or IL-17 in T cells (see FIG. 8), but this may have also been due in part to the fact that the T cells were minimally stimulated, as they were responding to autologous APC. These experiments did demonstrate the ability to detect small changes in T lymphocyte cytokine production among total PBMC. PBMC from eight healthy individuals were incubated with autologous APC in the presence of soluble control IgG or anti-PD-1 antibody to assess the effect of blocking PD-L1 signaling on T cell cytokine production. After five days, CD4 and CD8 T cells were identified and assayed for the presence or absence of intracellular cytokines. These experiments showed that soluble anti-PD-1 antibody at this concentration did not significantly affect intracellular production of IFN-γ, TNF-α, or IL-17 in T cells.

Example 4

Caspase Activity Levels were Measured in APC from Children with and without SLE

Cells were cultured as above, and PBMC were stained with Annexin V and propidium iodide (PI) (both from Becton Dickinson) to identify both dead and dying cells. After apoptotic cells were omitted from our analyses, the intracellular levels of caspases in living leukocytes were quantitated using fluorochrome derivatives of known caspase inhibitors which only bind at the active site (Immunochemistry Techologies, Inc.), thus revealing both caspase identity and activity level simultaneously in each individual cell. Using PBMC from five controls and two children with SLE, the mean fluorescence intensity (MFI) for each active caspase was measured, and results between controls and SLE compared using a 2-tailed t-test. Significance was assigned where $p<0.05$.

Figures 2, 9:
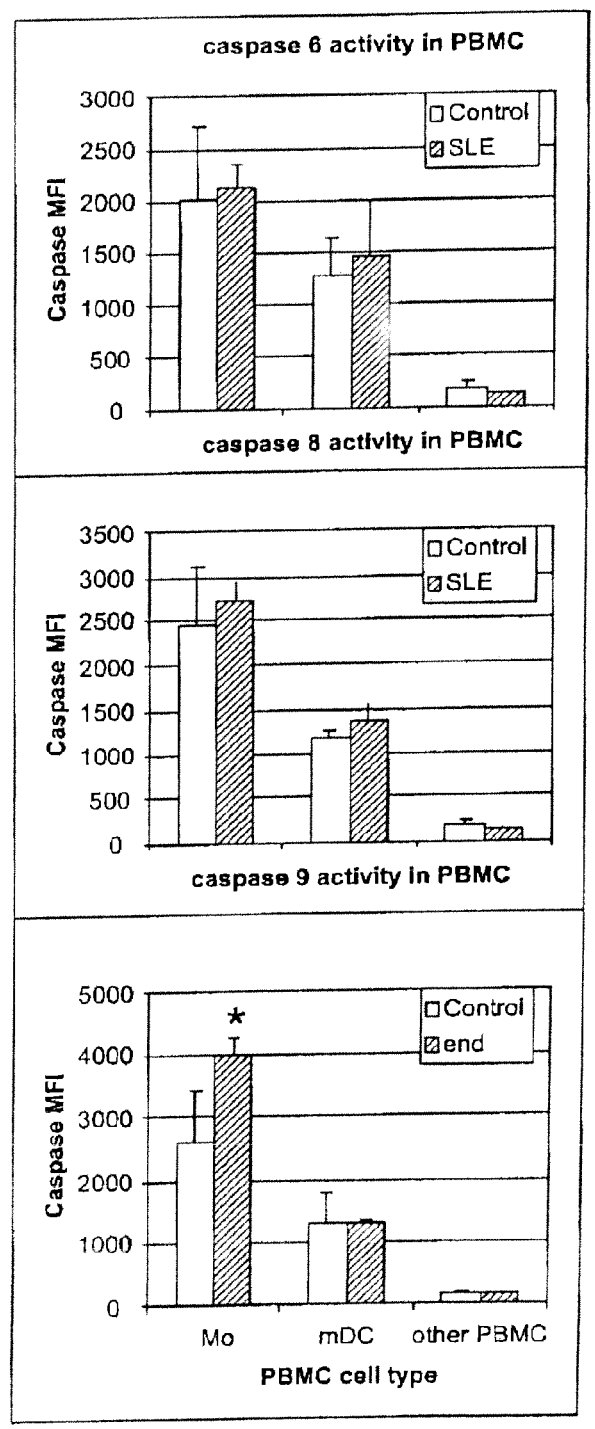

Surprisingly, for all of the eight caspases tested, it was found that enzyme activity levels in non-apoptotic cells exhibited the pattern: Mo>mDC>other PBMC, indicating an important role for caspases in normal Mo function (see FIG. 9). However, when comparing control Mo to SLE Mo, it was found that among individual caspases tested, only the activity of caspase-13 was significantly different between the two groups. The activity levels of caspases 1, 2, and 9 also appeared to be higher among SLE Mo. These experiments showed the baseline expression of caspases and their activity, level in human cells.

Example 5

Individual Caspases were Inhibited and APC Tested for Expression of PD-L1

Figure 10:
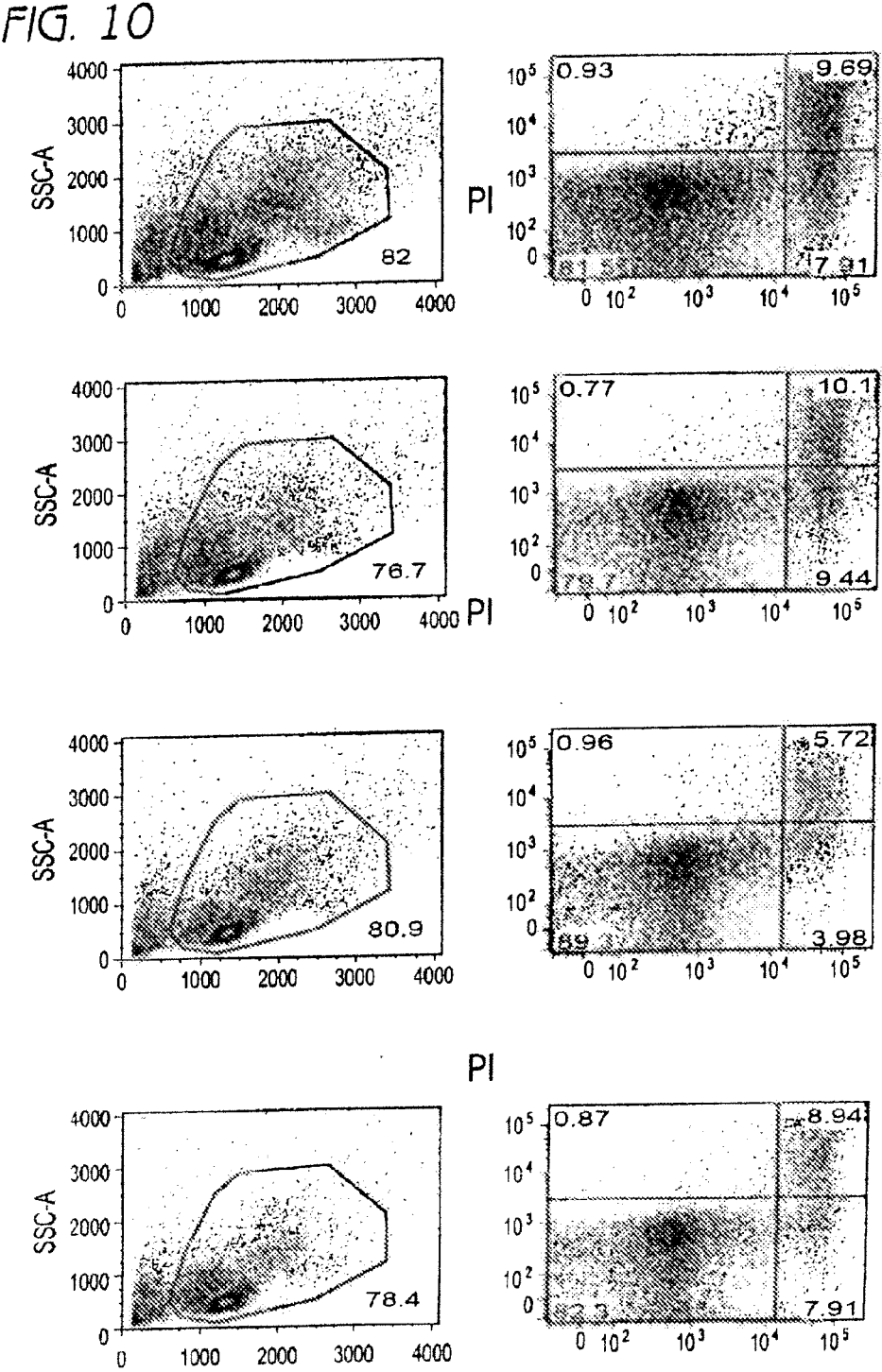
FIG. 10 shows the effect of caspase inhibitors on PBMC death and apoptosis. Treated cells were assayed for cell death and apoptosis using Annexin V and PI, as well as stained for cell-surface expression of PD-LI on APC. Note: sample results for only one set of control cells treated with OPH and Z-VAD-fmk are shown here, but studies were performed using both poly- and specific caspase inhibitors on multiple sets of PBMC.

This study examined the direct contribution of each caspase to the regulation of PD-L1 expression in vitro. Amino acids 70-180 of PD-L1 are shown in FIG. 10, with potential caspase cleavage sites marked by the four arrows. Caspase numbers are listed above each site in order of likelihood of cleavage.

In order to determine which caspase (or caspases) is responsible for downmodulation of PD-L1 during active lupus, the effects of specific caspase inhibitors on PD-L1 expression in human APC were tested (Table IV). Control and SLE PBMC were incubated for one day in the presence of the individual caspase inhibitors at doses ranging from 10 uM to 50 uM (R&D Systems), with the appropriate level of DMSO as the carrier control (0.5% final concentration). Treated cells were assayed for cell death and apoptosis using Annexin V and PI (example shown in FIG. 4), as well as stained for cell-surface expression of PD-L1 on APC.

TABLE IV

Specific caspase inhibitors and their targets.

| Inhibitor | Caspase target |
| --- | --- |
| Z-WEHD-fmk | 1 |
| Z-VDVAD-fmk | 2 |
| Z-DEVD-fmk | 3 (and 7) |
| Z-YVAD-fmk | 4 |
| Z-VEID-fmk | 6 |
| Z-IETD-fmk | 8 |
| Z-LEHD-fmk | 9 |
| Z-AEVD-fmk | 10 |
| Z-LEED-fmk | 13 |
| Z-VAD-fmk or OPH | Polycaspase inhibitor |

Figure 11:
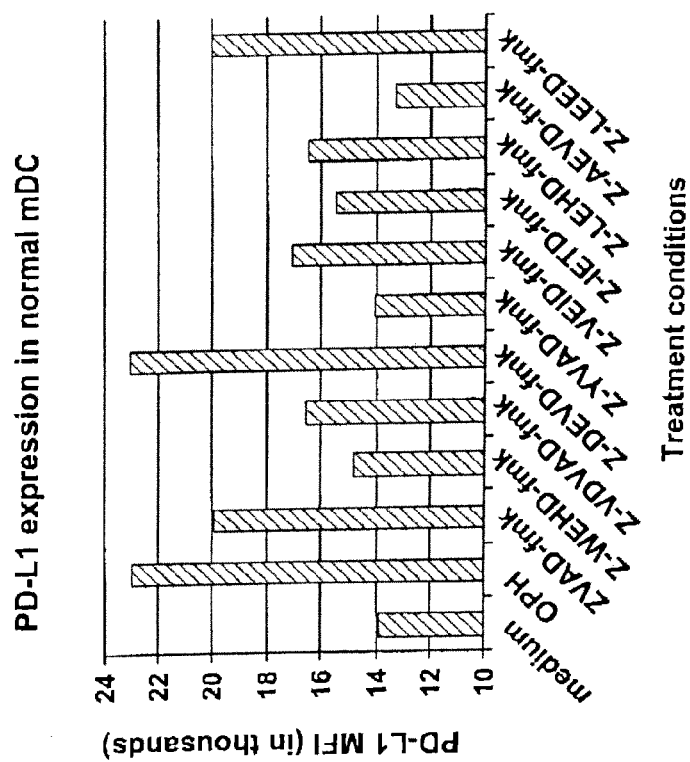
FIG. 11 shows the effect of specific caspase inhibitors on PD-L1 expression in mDC. This graph shows the PD-L1 quantitation results for one set of control mDC treated with various inhibitors.

The inhibitors enter living cells and bind irreversibly at the caspase active sites, preventing further proteolytic activity by the enzyme. After incubation with caspase inhibitors, PBMC were gated by forward and side scatter and analyzed for percent cell death and apoptosis using Annexin V and PI (see FIG. 10). It was found that treatment of PBMC with the specific caspase inhibitors was less potent for reducing cell death and apoptosis than the poly-caspase inhibitors, OPH and Z-VAD-fmk. It was also found that treatment of PBMC with low doses of the caspase-specific inhibitors (10-25 uM) did not affect PD-L1 expression by APC. However, higher doses of some caspase-specific inhibitors (50 uM), did alter PD-L1 levels, both in Mo and mDC (example shown in FIG. 11). Normal PBMC were incubated in medium with or without various caspase inhibitors, and PD-L1 protein levels assessed at day one. This graph shows the PD-L1 quantitation results for one set of control mDC treated with various inhibitors. Notably, using Method 1 above, it was observed that an elevation of active caspases 1, 2, 9, and 13 in SLE cells, with statistical significance demonstrated for caspase 13. In this set of experiments to determine the effect of these caspases on PD-L1 expression, we found that caspase-13 seemed to figure prominently in PD-L1 regulation (see Chart 6, under Z-LEED-fmk), confirming the usefulness of this multifaceted approach. Although the caspase-3 inhibitor (Z-DEVD-fmk) also greatly increased PD-L1 levels, caspase-3 acts as a master regulator of the caspase cascade and therefore it is not yet clear whether this enzyme acts directly on PD-L1 or via another caspase. Accordingly, these experiments demonstrate the direct contribution of each caspase to the regulation of PD-L1 expression in vitro.

Example 6

Downregulation of PD-L1 Protein Expression in Normal Mo by Induction of Apoptosis Healthy human PBMC were cultured and half of each sample were exposed to pro-apoptotic conditions—in this case, to withdrawal of serum from the culture medium. After 24 hours, cells were surface stained as above to identify Mo and to measure PD-L1 protein expression. It was found that among normal PBMC cultured in the absence of serum, PD-L1 protein levels dropped dramatically by 24 hours, as did the number of Mo expressing PD-L1 (Chart 7). The average PD-L1 MFI on Mo was reduced by more than half, while the percent of Mo expressing this negative costimulator dropped by one third. This PD-L1 profile observed in the context of serum withdrawal was remarkably similar to that obtained using cells from patients with active SLE, indicating that the loss of PD-L1 in lupus APC is indeed due to heightened caspase activity in these cells.

Figure 12:
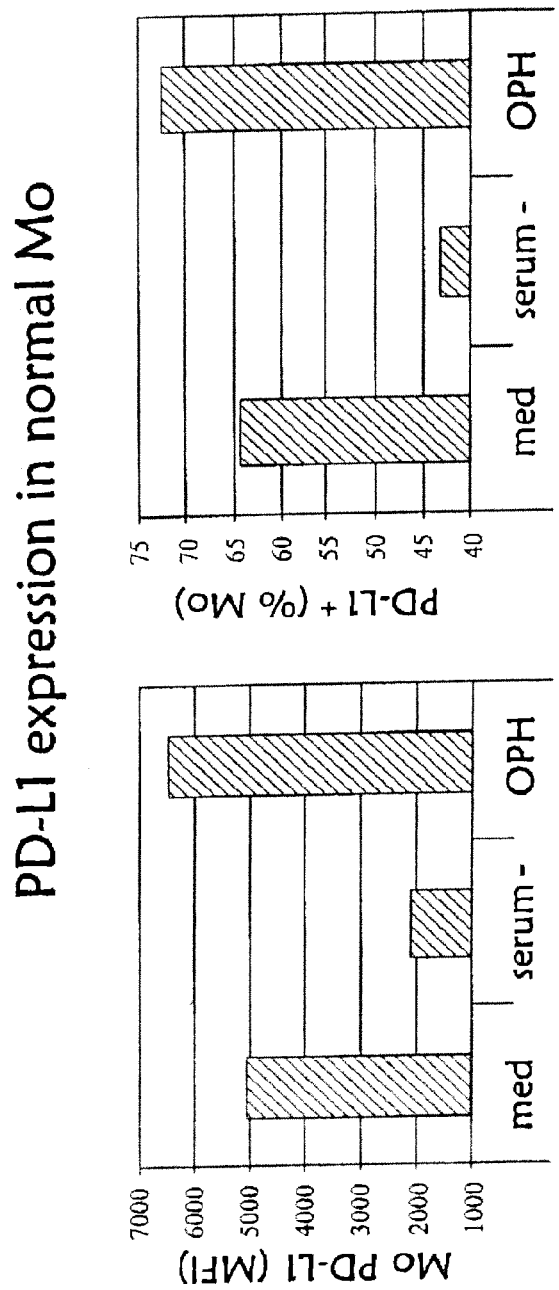
FIG. 12 shows the PD-L1 expression in Mo under pro- and anti-apoptotic culture conditions. Normal PBMC were cultured in standard medium containing serum (med), medium without serum (serum-) to increase apoptosis, or in medium containing 50 uM of polycaspase inhibitor (OPH) to decrease apoptosis. Bars reflect the mean values for Mo from two healthy individuals; left graph: PD-L1 MFI; right graph: percent of Mo expressing PD-L1.

The effect of various caspase inhibitors on PD-L1 expression in normal APC was also tested, as healthy cells can be made "lupus-like" by subjecting them to pro-apoptotic conditions (see FIG. 12). Normal PBMC were cultured in standard medium containing serum (med), medium without serum (serum-) to increase apoptosis, or in medium containing 50 uM of poly-caspase inhibitor (OPH) to decrease apoptosis. This system was used to test the effects of other pro-apoptotic conditions on caspase activation and PD-L1 expression, to determine if different apoptotic signals regulate PD-L1 differently. Such conditions include: UV irradiation, Fas:FasL signaling, and heat shock, as well as testing the direct effects of SLE serum on APC, as it has very recently been demonstrated that incubation of healthy leukocytes with lupus serum induces "classical" caspase-dependent apoptosis. These experiments provided evidence that the upregulation of caspase activity in normal cells should also lead to the downmodulation of PD-L1.

Example 7

Direct Cleavage of Human PD-L1 Protein In Vitro

As shown above, there exist significant differences in caspase activity between control and SLE APC, as well the PD-L1-enhancing effects of polycaspase inhibitors on human PBMC. These findings indicate that PD-L1 is directly cleaved by one or more active caspases.

Purified PD-L1 and control protein targets are incubated with individual caspases in the appropriate buffers under the conditions specified by the manufacturer. The resultant peptide products are fractionated by SDS-PAGE. Protein fragments are identified by size and gel-purified for further identification. Any molecules of interest are sequenced to confirm or refute potential PD-L1 caspase cleavage sites. Caspases of interest identified in these experiments are combined with other caspases in PD-L1 cleavage experiments, to determine whether a sequential or concurrent proteolysis of PD-L1 may occur during downmodulation of PD-L1 in living cells. We found that several caspases are capable of cleaving PD-L1 in vitro.

Example 8

Elevated Caspase Activity Inhibits Programmed Cell Death Ligand-1 Expression in Human Leukocytes and is Associated with Active SLE As discussed above, APC from patients with active SLE are deficient in PD-L1, but regain the ability to express this protein during disease remissions. Using flow cytometric analysis, the levels of endogenous caspase activity were measured in live APC from children with and without active SLE, and the effect of caspase inhibitors on expression of PD-L1 was tested.

Active SLE was associated with excessive leukocyte apoptosis, which was inversely correlated with PD-L1 protein levels on APC. Treatment with caspase inhibitors not only reduced leukocyte apoptosis, but also significantly increased expression of PD-L1 on both Mo and mDC. Although PD-L1 levels were elevated by caspase inhibitors, protein expression of CD80/86 was not increased, suggesting an overall decrease in the positive costimulatory capacity of these cells. Caspase inhibitors also increased PD-L1 levels on control and remission APC, suggesting a normal role for these proteases in regulation of this negative costimulatory molecule, and indicating that PD-L1 or its upstream signaling pathways are direct targets of caspases. This indicates that excessive leukocyte caspase activity in active SLE is linked to decreased PD-L1 protein expression on professional APC.

Example 9

Peripheral venous blood from volunteers was collected into heparin- or citrate-containing tubes (Vacutainer, Becton Dickinson) after informed consent was obtained. Clinical and laboratory data were collected for each sample at the time of blood draw (Table V).

bodies: anti-CD1c, (Miltenyi), anti-CD3, anti-PD-L1 (eBioscience), anti-CD11b, anti-CD11c, anti-CD14, anti-CD-86, anti-PD-L2 (Pharmingen/BD Biosciences), anti-CD45RO, anti-CD80, anti-CD83, and/or anti-HLA-DR (BioLegend), with isotype-matched, fluorochrome/biotin-labeled irrelevant monoclonal antibodies as controls. All samples were blocked using 0.5% human serum and anti-FcR antibody (Miltenyi) during staining. Cells were fixed using 2% paraformaldehyde in PBS after preliminary experiments indicated no effect of cell fixation on expression levels of PD-L1 and other surface markers. To assess apoptosis, some cultures were stained in parallel with Annexin V and propidium iodide (PI) (both from Becton Dickinson) as per the manufacturer's instructions. Flow cytometry was performed using a FACSCalibur or LSR II cytometer (Becton Dickinson), and data were analyzed using FlowJo software (Macintosh Version 6.3).

TABLE V

| SLE Subject # | Gender | Age at draw (years) | Disease duration (years) | Low C3 &/or C4 at draw | Lymphopenia at draw | SLE status[b] | I.V. steroids[c] | I.V. cyclophosphamide | Daily oral MMF (mg) | Daily oral HCQ | Daily oral pred (mg) | Weekly oral MTX (mg) |
|---|---|---|---|---|---|---|---|---|---|---|---|---|
| 1 | F | 15.5 | >5[d] | na | – | stable | — | — | — | + | — | — |
| 2 | F | 12.5 | <1 | – | – | stable | 2 mo prior | — | — | + | 20 | — |
| 3 | F | 15.9 | <1 | + | – | stable | — | — | — | – | ≤10 | — |
| 4 | F | 18.7 | 1-3 | + | – | stable | 3 mo prior | 3 mo prior | — | + | — | — |
| 5 | F | 7.7 | <1 | na | – | stable | — | — | — | + | 60 | — |
|   |   | 8.1 | 1-3 | – | – | stable | 1 mo prior | — | 1000 | + | 15 | — |
| 6 | F | 16.1 | 3-5 | na | na | stable | — | — | — | + | ≤10 | — |
|   |   | 17.3 | >5 | – | – | stable | — | — | — | – | — | — |
| 7 | F | 13.1 | 1-3 | – | + | flare | — | — | — | + | ≤10 | — |
|   |   | 15.4 | 3-5 | – | + | stable | >12 mo prior | — | >6 mo prior | + | ≤10 | — |
| 8 | F | 15.7 | 3-5 | + | – | flare | — | — | — | + | — | 15 |
|   |   | 17.5 | >5 | – | – | stable | — | — | — | + | — | 20 |
| 9 | F | 16.0 | 1-3 | + | + | flare | — | — | — | + | ≤10 | 25 |
|   |   | 18.9 | 3-5 | – | + | stable | — | — | — | + | ≤10 | 2.5 |
|   |   | 21.2 | >5 | + | – | stable | — | — | — | + | ≤10 | — |
| 10 | F | 10.7 | <1 | + | – | stable | — | — | — | + | — | — |
|   |   | 11.6 | 1-3 | + | – | flare | — | — | — | + | — | — |
| 11 | F | 11.2 | <1 | + | + | flare | 1 mo prior | 1 mo prior | — | + | 30 | — |
| 12 | F | 12.1 | <1 | + | + | flare | — | — | — | + | ≤10 | — |
| 13 | M | 15.0 | 1-3 | – | – | flare | — | — | — | + | ≤10 | 15 |
| 14 | F | 15.6 | >5 | + | + | flare | — | — | — | + | ≤10 | — |
| 15 | F | 17.2 | 1-3 | + | + | flare | — | — | — | + | 20 | — |
| 16 | F | 6.4 | 1-3 | + | – | flare | — | — | — | – | — | — |
| 17 | F | 9.9 | <1 | + | – | flare | — | — | — | – | — | — |
| 18 | F | 15.4 | <1 | na | – | flare | — | — | — | – | — | — |
| 19 | F | 16.6 | <1 | na | – | flare | — | — | — | – | — | — |

PBMC were isolated by density centrifugation over a Ficoll-Paque gradient (Amersham), frozen in heat-inactivated AB human serum (Valley Biomedical) with 7% DMSO (Sigma), and stored in liquid nitrogen until use. In preliminary studies, PBMC samples were split into frozen and fresh aliquots and tested to confirm a lack of effect of freeze-thaw on our experimental outcomes.

PBMC were thawed, washed, and diluted to $1-2\times10^6$ cells/ml in culture medium consisting of RPMI 1640 with L-glutamine (CellGro), 10% heat-inactivated NB human serum (Valley Biomedical), 1% penicillin/streptomycin (CellGro), and 0.1% beta-mercaptoethanol. Cells were plated in round-bottom 96-well plates (Corning Costar) and incubated at 37° C. in a humidified cell chamber with 5% CO2. Some wells were treated with pan-/poly-caspase inhibitors at the time of plating: 50 uM Q-Val-Asp-(non-o-methylated)-OPh (OPH) or Z-Val-Ala-Asp-(beta-o-methyl)-fluoromethylketone (Z-VAD) (both from R&D Systems), or DMSO as the carrier control (0.5% final concentration).

At the timepoints indicated, cells were surface-stained using fluorochrome- or biotin-conjugated monoclonal anti- Populations were compared using a 2-tailed t-test, and significance assigned where $p<0.05$. A total of 26 PBMC samples were collected from 19 SLE patients ranging in age from 6-21 years old (mean=14.3+/−3.7); 13 of these samples were obtained from patients with active (recurrent or newly diagnosed) SLE and designated "flare" samples; 13 were obtained from patients with inactive SLE and designated "remission" samples; (Table I). Control PBMC were obtained from 17 healthy volunteers ranging in age from 6-23 years old (mean=16.5+/−5.3); age was not significantly different between the SLE and control groups. Female subjects comprised 18/19 of the SLE patients and 14/17 of the controls.

After one day of culture in the absence of exogenously added stimuli, PD-L1 was expressed on a proportion of $CD3^-$ cells from healthy subjects, but there was near-complete absence of PD-L1 on PBMC from patients with active SLE (FIG. 1A). $CD3^-$ PBMC from patients in lupus remission had regained the ability to express PD-L1.

To further characterize these $CD3^-$ PD-L1+cells, levels of several APC surface markers in control PBMC were and it was found that the PD-L1+cells were of myeloid lineage by staining for CD14 (FIG. 1B). These CD14$^{low}$ and CD14$^{hi}$ populations expressed CD11c, CDIIb, CD45RO, and HLA-DR, and corresponded to CD 1c$^{+/-}$ CD80/CD86$^{hi}$ mDC and CD1c$^-$ CD80/CD86$^{low}$ Mo populations, respectively, demonstrating that PD-L1 was primarily expressed on professional APC (FIG. 1 C). Similar to prior findings there was not found a significant amount of CD83 on these cells, supporting the idea that the mDC in these cultures were phenotypically immature. APC profiles in PBMC from patients in SLE flare or remission were similar to those of controls.

Figure 2B:
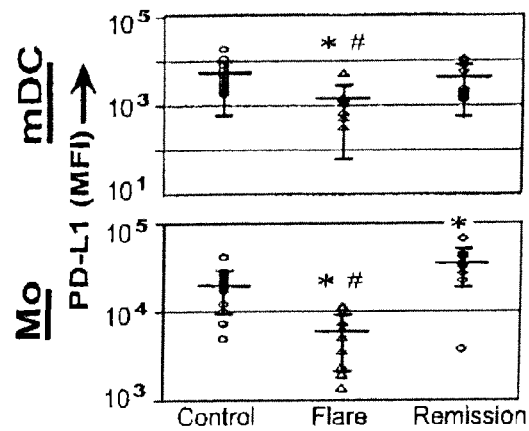
Figure 2C:
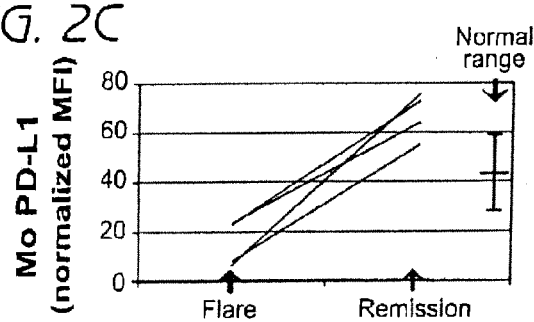
Figure 2D:
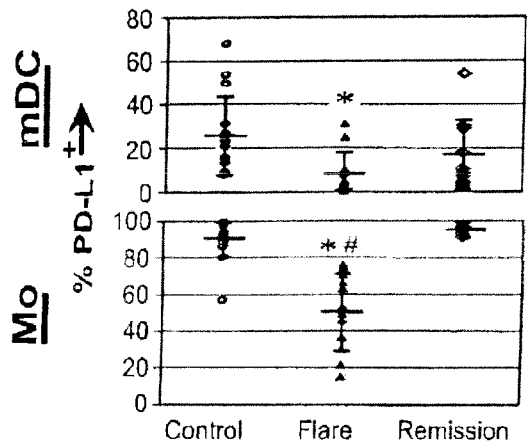
Figure 5A:
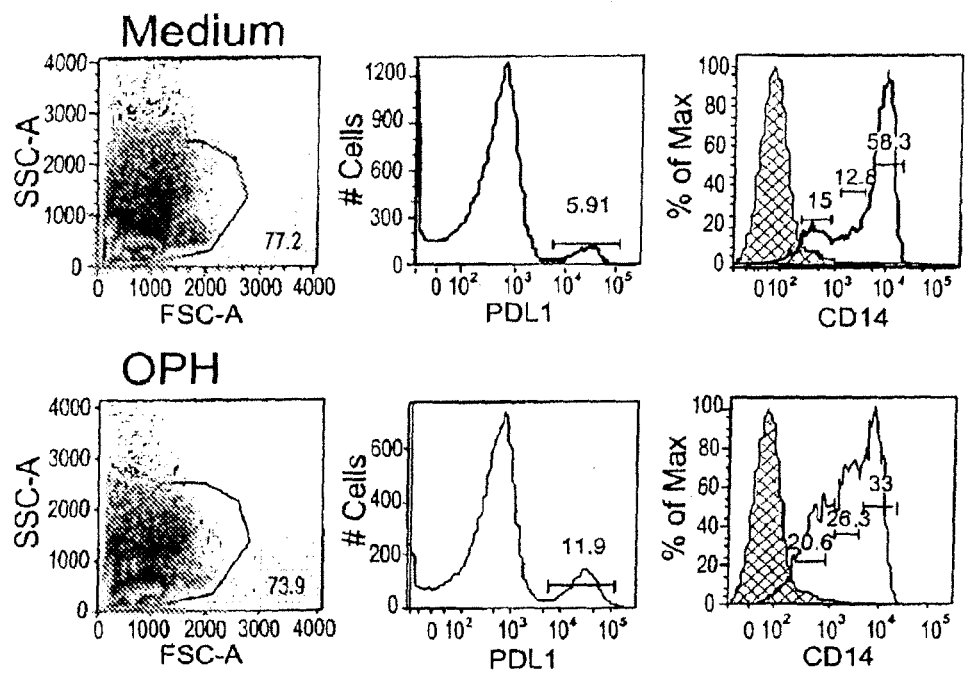
FIGS. 5A-5D show that other APC surface markers are not globally upregulated by caspase inhibitors.
Figure 5B:
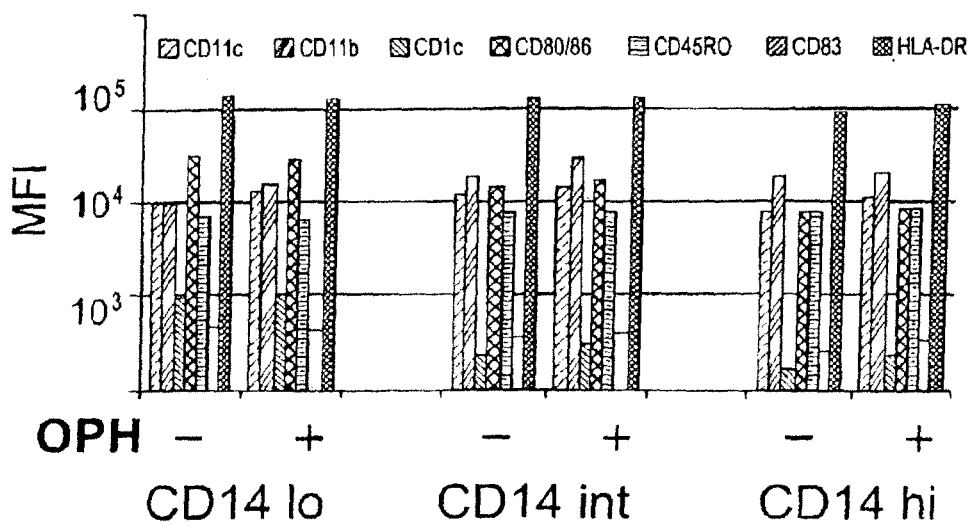
Figure 5C:
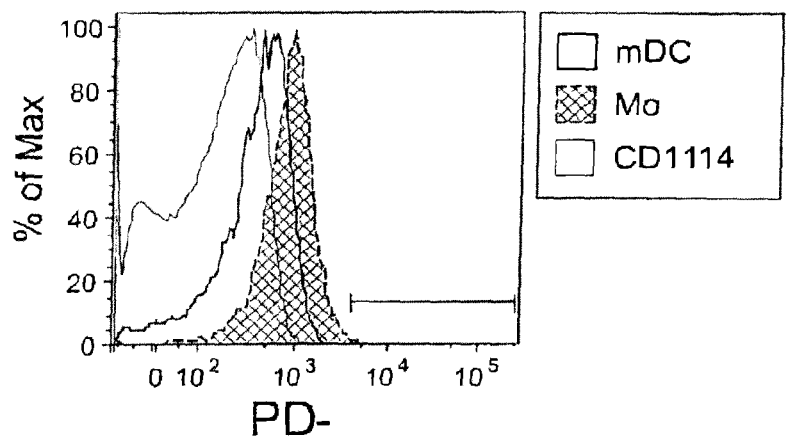
Figure 5D:
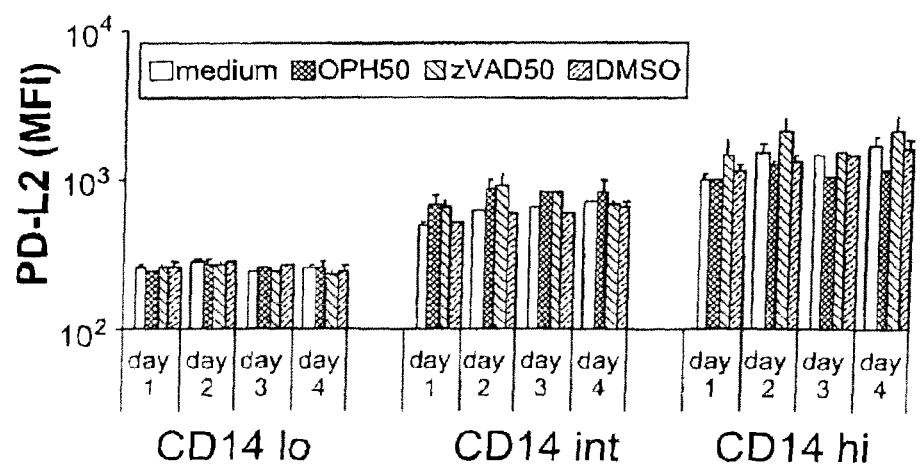
Figure 6:
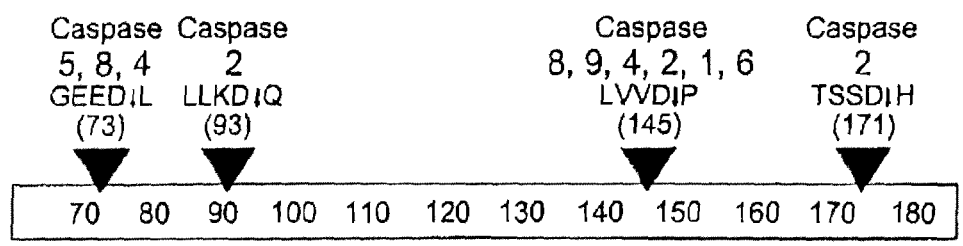
FIG. 6 shows that potential cleavage sites for caspases 1-9 fall between PD-L1 amino acids 70-180. Caspases are listed in order of greatest likelihood of cleavage at that site based on correlation with their known consensus recognition sequences.

To assess levels of PD-L1 on immature mDC and Mo, PBMC were cultured as above and APC identified by double-staining for CD11c and CD14 (FIG. 2A). In comparison to APC from healthy controls, it was found that both immature mDC and Mo from children with active SLE failed to upregulate PD-L1, while APC from children in lupus remission expressed normal or increased amounts of this negative costimulator (FIG. 2A). These findings were reproducible using immature mDC and Mo from multiple individuals (FIG. 2B). Compared to control APC, mean PD-L1 expression was more than three-fold lower in immature mDC and Mo from children in SLE flare, but nearly two-fold higher in Mo from children in SLE remission, indicating that this negative costimulator may play a role in inhibiting the autoreactive immune response. In support of this concept, serial samples drawn from four patients at different times revealed inverse correlation of PD-L1 expression with SLE disease activity (FIG. 2C), with lower levels during lupus flares and higher levels during remissions. Not only were PD-L1 levels significantly lower in SLE flare, but these PBMC also had a lower percentage of APC expressing PD-L1. Two- to three-fold fewer mDC and nearly half as many Mo were PD-L1$^+$ in SLE flare samples as compared to APC from healthy controls and patients in SLE remission (FIG. 2D).

Figures 3, 9:
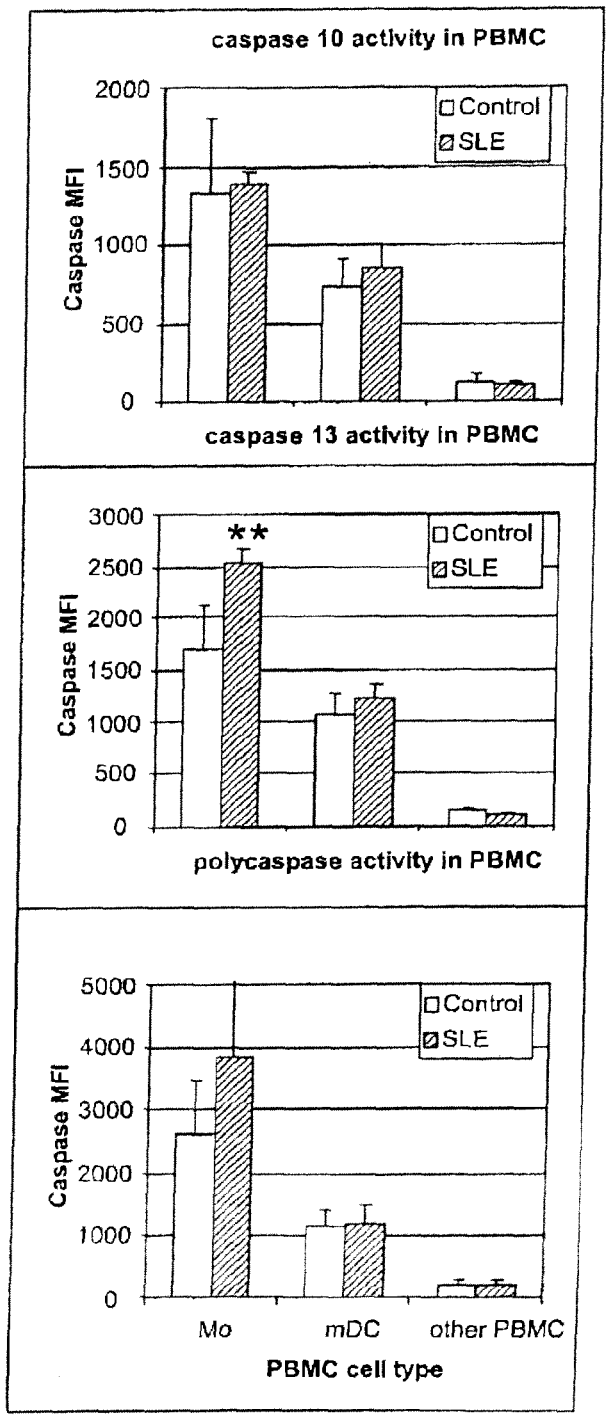

To rule out the possibility that APe from patients with active SLE were merely delayed in upregulation of PD-L1, expression of this protein was measured over a five-day time period (FIG. 3). Normal APC expressed little PD-L1 at initiation of culture, but levels rapidly increased over time, with peak PD-L1 expression in both mDC and Mo by day three (FIGS. 3A and 3C). These findings are in agreement with previous work which showed that purified normal human Mo expressed very little PD-1 or PD-L2 upon initial isolation, but spontaneously upregulated PD-L1 after 24 h of culture. As was observed in short-term cultures, it was found that APC from patients in SLE remission expressed PD-L1 at or above normal levels; the kinetics of PD-L1 induction in these cells were similar to those of control cells (FIGS. 3A and 3C). In contrast to control APC, immature mDC and Mo from children with active SLE expressed abnormally low levels of PD-L1 throughout the timecourse, refuting the idea that the low PD-L1 observed in day one cultures was merely due to delayed expression.

Although mean PD-L1 expression was consistently lower in active SLE throughout the timecourse, this was not merely due to a lower proportion of APC expressing PD-L1. The total number of mDC and Mo was quantified at each timepoint, as were the number of cells expressing PD-L1, and it was found that the total numbers of mDC and Mo were not significantly different between samples over time (FIGS. 3B and D). In active SLE, slightly fewer mDC expressed PD-L1 over the entire culture period (FIG. 3B), but the proportion of Mo expressing PD-L1 was similar to that of controls after day one (FIG. 3D).

The finding that immature mDC and Mo failed to upregulate PD-L1 in active SLE has significant implications for pathologic conversion of APC to an immunogenic state. Immature mDC ingest apoptotic bodies and cross-present Ags to cytotoxic T cells and lack of P-1 signaling in vivo results in DC-mediated CD8$^+$ T cell priming rather than tolerization. Therefore, in the absence of PD-L1, autoantigen presentation by lupus mDC may result in T cell activation, rather than tolerogenesis.

In addition to implications for augmented T effector activity, PD-L1 deficiency may also lead to abnormal T regulatory cell (Treg) function and/or development. Prior work revealed that PD-L1 was necessary for the suppressive activity of classic CD4$^-$CD25$^+$ Treg in an animal model of GVHD, and that costimulation of naive CD4$^+$ T cells with an anti-CD3 antibody plus PD-L1-Ig fusion protein resulted in formation of Trl regulatory cells.

It was observed that PBMC from children in SLE flare had the highest level of apoptosis (FIG. 4A), and in all cultures, apoptosis was reduced by the addition of OPH, a potent pan-caspase inhibitor (FIG. 4B). It was found that OPH also significantly increased PD-L1 expression in Mo of all three groups compared to untreated (FIG. 4C), and doubled the mean percentage of Mo expressing PD-L1 in SLE flare (from 45% to 97%). With respect to immature mDC, OPH increased PD-L1 expression in all three groups two- to three-fold (p<0.02), and more than doubled the mean percentage of mDC expressing PD-L1 in all three groups (P<0.013). This concentration of OPH was not sufficient to completely normalize the excessive apoptosis (FIG. 4B) nor the deficient Mo PD-L1 expression in SLE flare (FIG. 4C), revealing an inverse correlation between apoptosis and PD-L1 (FIG. 4D). This reciprocal relationship between caspase activity and Mo PD-L1 expression also held true for all PBMC treated with another caspase inhibitor (Z-VAD).

Figure 7:
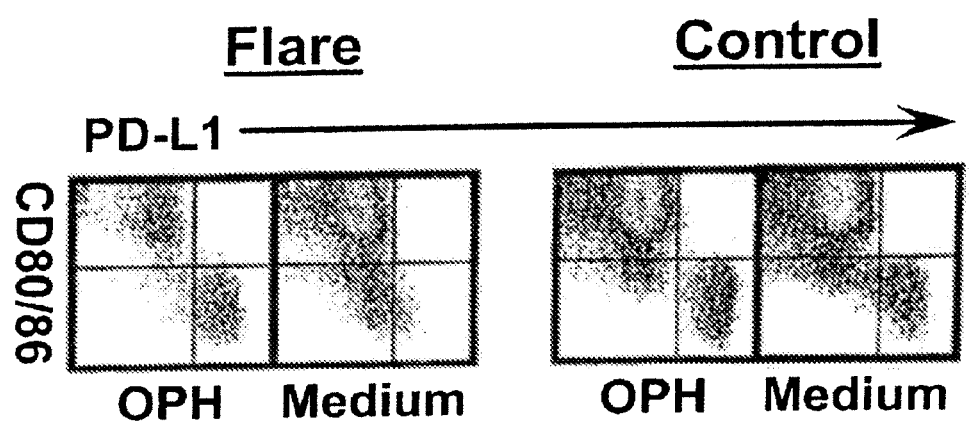
FIG. 7 shows the costimulatory potential of SLE flare APC could be normalized by inhibition of caspases PBMC were cultured for one day and stained for the costimulatory molecules C080, CD86, and PD-L1. CD80/86 levels are similar in control and SLE flare APC, but SLE flare cells lack concurrent PD-L1 expression. Treatment of PBMC with OPH increased PD-L1 levels in control cells and restored normal levels of PD-L1 in SLE flare cells. PBMC from a second healthy child and from a patient in SLE remission behaved the same as the normal control.

APC was examined for expression of CD80 and CD86 in the presence and absence of OPH to determine the potential consequences of decreased PD-L1 in active SLE. In PBMC from healthy controls, CD80/86+ APC were clearly PD-L1$^+$ in the absence of exogenous stimuli, and upregulated PD-L1 further after treatment with OPH (FIG. 7). In contrast, untreated APC from children with active lupus were markedly PD-L1-deficient without any apparent deficiency in expression of CD80/86; suggesting a high level of positive costimulatory capacity in these cells. In the presence of OPH, PD-L1 levels in SLE flare APC approached those of untreated control cells (FIG. 7), indicating that the abnormal balance of costimulatory signaling in lupus APC could be ameliorated by inhibition of caspases.

Insults which promote apoptosis, such as drugs, infection, or UV irradiation, may inhibit APC from expressing PD-L1 due to activation of caspases. PD-L1-deficient APC could then play a role in triggering lupus-like symptoms by presenting apoptosis-related antigens in an inflammatory context, providing a final common pathway for breakdown of peripheral tolerance in SLE. Pristane, which causes a lupus-like syndrome when injected into normal mice, and chlorpromazine, which causes a lupus-like syndrome in humans, activate caspases and trigger apoptosis in leukocytes. Infliximab, which can cause a lupus-like syndrome in susceptible individuals, was recently shown to promote caspase activation and apoptosis in human macrophages. The above experiments showed that the failure of APC to upregulate PD-L1 contributes to abnormal T lymphocyte regulation and loss of peripheral tolerance in SLE.

Example 10

Paediatric donors with and without SLE were recruited under a research protocol. Peripheral venous blood was collected into heparin- or citrate-containing tubes (Vacutainer, Becton Dickinson, N.J., USA) after written informed consent was obtained from the child and/or parent/guardian. Blood samples were centrifuged and plasma aliquots. Peripheral blood mononuclear cells (PBMC) were isolated by density centrifugation over a Ficoll-Paque gradient (Amersham, Uppsala, Sweden), frozen in heat-inactivated AB human serum (Valley Biomedical, Winchester, Mass., USA) with 7% DMSO (Sigma, St. Louis, Mo., USA), and stored in liquid nitrogen until use. In preliminary experiments, PBMC samples from four unique donors were split into frozen and fresh aliquots, and evaluated by flow cytometry to confirm, a lack of effect of freeze-thaw on expression levels of PD-L1 (P≥0.7).

Clinical and laboratory data were collected for each individual, and all but one of the lupus patients fulfilled the current ACR classification criteria for SLE. As this was a retrospective study, the European Consensus Lupus Activity Measurement (ECLAM) was calculated for all patient samples where information was available (n=24); ECLAM scores ranged from 0 to 6.5, with a mean±S.D. of 2.5±2.0. As no patient had documentation of seizures, psychosis, cerebrovascular accident, cranial nerve disorder, visual disturbance, myositis, pleurisy, pericarditis, intestinal vasculitis or peritonitis at the time of blood draw, we used a modified scoring system to group patients with respect to disease activity, consisting of these remaining categories: mucocutaneous disease (rash, alopecia, mucosal ulcers and finger nodules), arthritis, haematuria, thrombocytopenia and hypocomplementaemia. In addition, we used lymphopenia, rather than leucopenia, as a sensitive measure of active paediatric SLE. Several samples were chosen at random and also assayed for PBMC apoptosis and/or plasma levels of IFN-α, as these markers are strongly linked to SLE disease activity. PBMC apoptosis was considered to be abnormally high if outside the bounds of the 99.95% CI of control cells (PBMC from seven healthy children tested, data not shown) and plasma IFN-α levels were considered to be abnormal if ≥5 times the upper limit of normal (six healthy children tested).

As the clinical assessments were gleaned from chart notes written by a panel of different physicians, the objective laboratory data were weighted more heavily in the final determination, with each abnormal laboratory value assigned 2 points, and each abnormal clinical finding assigned 1 point. A total disease activity score of ≥4 points was felt to represent active disease, and called 'flare', while a score of <4 was felt to represent inactive disease, and called 'remission'. This modified scoring system has the limitation that it has not been formally validated; however, there are no validated disease activity scoring systems for paediatric SLE. Moreover, when this modified scale was used to categorize patients into flare and remission groups, the mean ECLAM scores and anti-dsDNA antibody levels were found to be significantly different between the two groups (Table I), suggesting the potential utility of this approach.

PBMC were thawed, washed and diluted to $1-2\times10^6$ cells/ml in culture medium consisting of RPMI 1640 supplemented with L-glutamine (CellGro, Herndon, Va., USA), 10% heat-inactivated AB human serum, 1% penicillin/streptomycin (CellGro) and 0.1% β-mercaptoethanol. Cells were plated in round-bottom 96-well plates (Corning Costar, Corning, N.Y., USA) and incubated at 37° C. in a humidified cell chamber with 5% $CO_2$. At the time points indicated, PBMC were surface-stained using various fluorochrome- or biotin-conjugated mAbs, including: anti-CD1c, (Miltenyi, Auburn, Calif., USA), anti-CD3, anti-PD-L1 (eBioscience, San Diego, Calif., USA), anti-CD11b, anti-CD11c, anti-CD14, anti-CD-86, anti-PD-L2 (Pharmingen/BD Biosciences), anti-CD45RO, anti-CD80, anti-CD83 and/or anti-HLA-DR (BioLegend, San Diego, Calif., USA), with isotypematched, fluorochrome-/biotin-labelled irrelevant mAbs as controls.

All samples were blocked using 0.5% human serum and anti-FcR antibody (Miltenyi) during staining. After staining, PBMC were fixed using 2% paraformaldehyde in PBS after preliminary experiments indicated no effect of cell fixation on expression levels of PD-L1 or other surface markers (data not shown). Some cultures were stained in parallel with Annexin V and propidium iodide (PI) as per the manufacturer's instructions (both from Becton Dickinson) and apoptosis assessed by enumerating the percent of Annexin V-positive PBMC per culture. Flow cytometry was performed using an LSR II cytometer (Becton Dickinson), and the data were analysed using Flow Jo software (Tree Star, Inc., Ashland, Oreg., USA).

Populations were compared using a two-tailed t-test and significance assigned where $P<0.05$. Due to the fact that some patients had more than one blood draw and were therefore overrepresented in the data set, statistical analyses were repeated using multivariate logistic generalized estimating equations (GEEs), to account for multiple observations in some individuals. Results of GEE analyses confirmed $P<0.05$ between populations as identified by t-test.

A total of 26 PBMC samples were collected from 19 unique SLE patients ranging in age from 6 to 21 yrs (mean±S.D.=14.3±3.7). Clinical and laboratory data for these blood draws are summarized in Table I. Overall, 12 samples were obtained from patients with active (recurrent or newly diagnosed) SLE and categorized as 'flare' samples, while 14 were categorized as 'remission' samples, as outlined above. Patient age was not significantly different between the SLE flare (13.8±3.1) and remission (14.7±4.2) groups, and there were no statistically significant differences between the groups with respect to medication usage. Control PBMC were collected from 15 healthy volunteers ranging in age from 6 to 23 yrs (15.7±5.2); patient age and gender composition were not significantly different between the control and SLE groups. Females comprised 18/19 of the SLE patients and 12/15 of the controls.

To test the hypothesis that PD-L1 expression is abnormal on lupus APC, primary human PBMC were cultured for 1 day in the absence of exogenously added stimuli and PD-L1 levels measured using four-color multiparametric flow cytometry. Consistent with prior findings in normal human leucocytes, we observed virtually no PD-L1 protein on $CD3^+$ cells, but PD-L1 was expressed on a proportion of $CD3^-$ cells from a healthy subject (FIG. 1A). In contrast, there was near-complete absence of PD-L1 on PBMC from a patient with active SLE. Surprisingly, $CD3^-$ cells from the same patient during lupus remission had regained the ability to express normal levels of PD-L1. This pattern was reproducible using PBMC from multiple individuals (see below).

To characterize the $CD3^-$ cells expressing PD-L1, we assessed levels of several surface markers on normal PBMC and found that the PD-L1$^+$ cells naturally segregated into CD14-low/negative ($CD14^{lo}$) and CD14-high ($CD14^{hi}$) populations (FIG. 1B), demonstrating that PD-L1 was primarily expressed by APC of myeloid lineage, consistent with published data. Examination of the $CD14^{lo}$ and $CD14^{hi}$ APC subsets for CD11c, CD11b, CD1c, CD45RO and HLA-DR revealed expression patterns consistent with immature mDC and Mo, respectively (FIG. 1C). Similar to a prior report, we did not observe a significant amount of CD83 on these cells, supporting the idea that the mDC in these cultures were phenotypically immature.

To confirm abnormal PD-L1 levels on lupus APC, PBMC were cultured as above and immature mDC and Mo identified by co-staining for CD14 and CD11c (FIG. 13A). As noted, we found that both immature mDC and Mo from children with active SLE failed to up-regulate PD-L1, while APC from children in lupus remission expressed normal or increased levels of this negative costimulator (FIG. 13B). As the CD14$^{lo}$CD11c$^+$ populations in PBMC may have been comprised of a heterogenous mix of differentiating Mo and early mDC, we used the cell surface marker CD1c (BDCA-1) to specifically identify Type I mDC. Gating for CD14$^{lo}$ CD11c$^+$ CD1c$^+$ cells revealed PD-L1 expression consistent with that of the CD14$^{lo}$ CD11c$^+$ population as a whole, confirming the utility of this method for measuring PD-L1 levels on immature mDC (FIG. 13C).

These findings were reproducible and statistically significant for immature mDC and Mo from multiple individuals (FIG. 13D-F). Compared with control APC, mean PD-L1 expression was more than 3-fold lower on immature mDC and Mo from children in SLE flare, but nearly 2-fold higher on Mo during SLE remission (FIG. 13D). To correct for potential inter-experiment variation, the PD-L1 MFI for each set of APC was normalized to background levels, using the PD-L1 MFI of the CD14$^-$ CD11c$^-$ cells as the denominator for each sample. However, mDC and Mo from patients in SLE flare remained significantly PD-L1-deficient as compared with both normal and remission APC (FIG. 13E). Not only were PD-L1 protein levels lower on SLE flare APC, but there were also lower percentages of cells expressing PD-L1 (FIG. 13F). Compared with controls, PD-L1 was expressed on nearly 70% fewer SLE flare mDC and nearly 50% fewer Mo. In contrast, the percentages of PD-L1$^+$ APC in lupus remission samples were not significantly different than in controls, consistent with the idea that this negative costimulator may play a role in inhibiting the autoreactive immune response. In support of this concept, serial samples drawn from four patients at different times revealed an inverse correlation between Mo PD-L1 expression and disease activity, with lower levels during SLE flares and higher levels during remissions (FIG. 13G).

To rule out the possibility that APC from patients with active SLE were merely delayed in up-regulation of PD-L1, we measured expression of this protein over a 5 day culture period. Normal APC expressed little PD-L1 at initiation of culture, but levels rapidly increased over time, with peak PD-L1 expression in both immature mDC and Mo by days 1-2, and return to baseline by day 5. In contrast, immature mDC and Mo from children with active SLE expressed abnormally low levels of PD-L1 throughout the time course, refuting the idea that the low PD-L1 observed in day 1 cultures was merely due to delayed surface expression of this protein. As in short-term cultures, APC from children in SLE remission exhibited normal or elevated levels of PD-L1, suggesting a potential functional association between PD-L1 expression and disease activity.

In contrast to PD-L1, staining of control PBMC for the related negative co-stimulator, PD-L2, revealed a nearly negligible level of protein expression that did not change over 4 days of culture. These findings are in agreement with previous work that showed that purified Mo from healthy adult volunteers expressed virtually no PD-L1 or PD-L2 upon initial isolation, and spontaneously up-regulated only PD-L1 after 24 h of culture.

To determine whether the defect in lupus flare APC was specific to PD-L1, we measured the level of positive co-stimulatory molecules (a combination of CD80 plus CD86) on PBMC from children with and without SLE. We found that although immature mDC and Mo were clearly PD-L1-deficient during SLE flare, they retained the ability to express CD80/CD86 (FIG. 14), congruent with prior studies that revealed normal or elevated levels of these proteins on mDC and Mo from patients with SLE. Taken together, these observations suggest that the inability of lupus APC to express PD-L1 cannot be attributed to a global decrease in costimulatory molecule expression during SLE flare, and that loss of the negative PD-L1 signal is not associated with or compensated for by a decrease in positive co-stimulatory signals.

Figure 14:
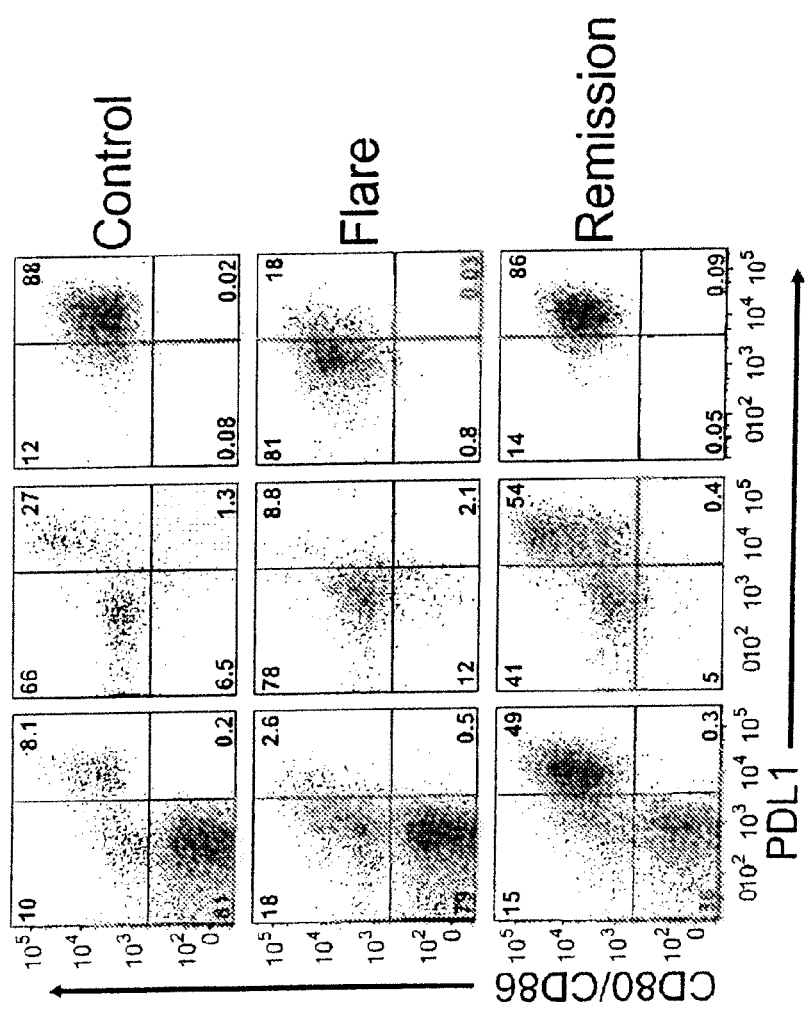
FIG. 14 shows lupus flare APC express positive co-stimulatory molecules. PBMC were cultured for 1 day and gated for APC as given earlier. Compared with control cells (top row), SLE flare APC (middle row) lacked PD-L1 and the $CD80/86^{hi}$ subset of mDC. In contrast, SLE remission cells (bottom row) expressed both PD-L1 and CD80/86 in a pattern similar to that of controls (numbers in each graph represent the percentage of cells in each quadrant). Results are representative of two separate experiments using PBMC from three healthy controls, two SLE flare and two SLE remission.
Figure 15:
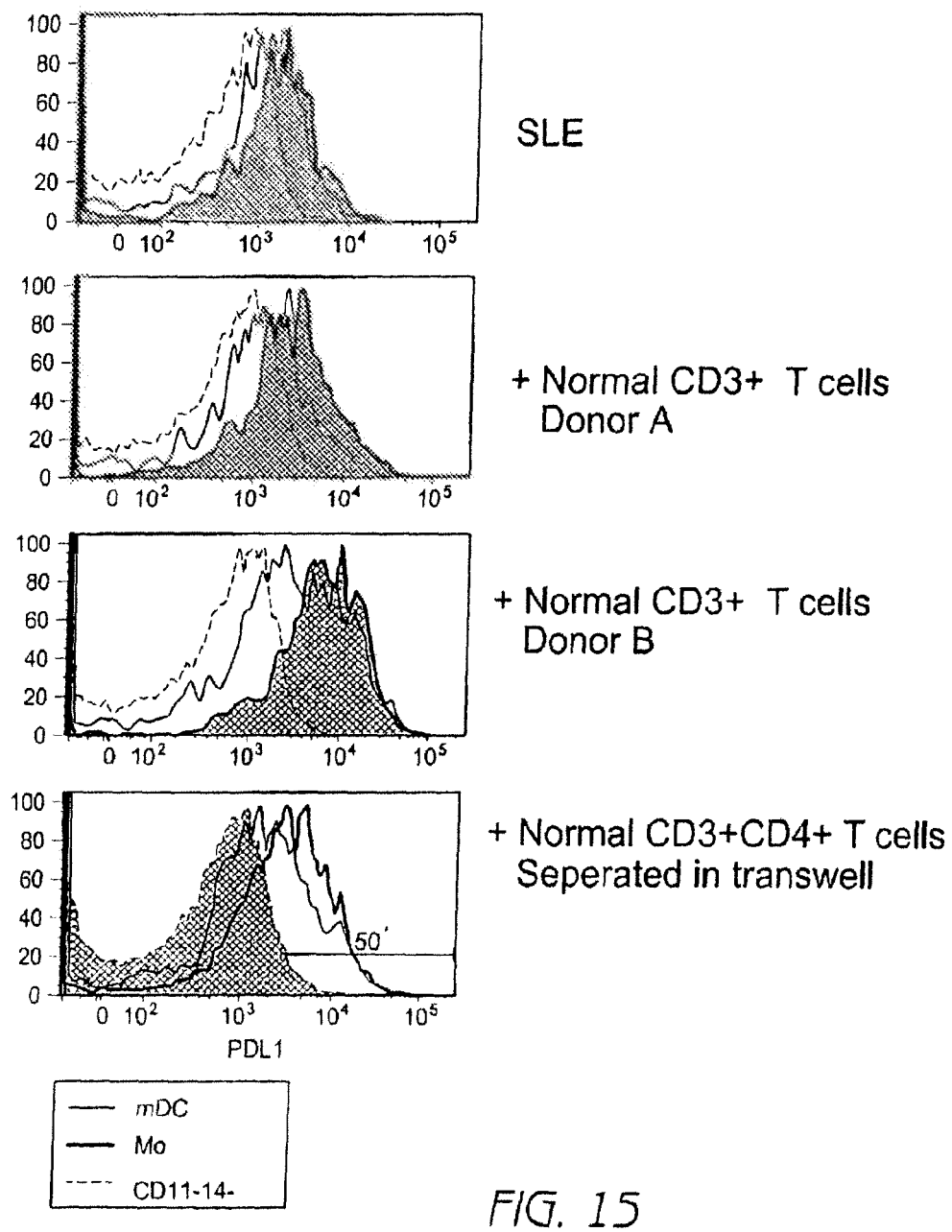
FIG. 15 shows PD-L1 expression on SLE Mo and mDC can be induced by CD4+ T cells from a healthy donor. CD3+CD4+ T lymphocytes were isolated from healthy PBMC by florescence activated cell sorting and added to total PBMC from an SLE patient with active disease. After one day in culture, PD-L1 expression on CD11c+CD14+ Mo and CD11c+CD14lo mDC was assayed by flow cytometry.
Figure 16:
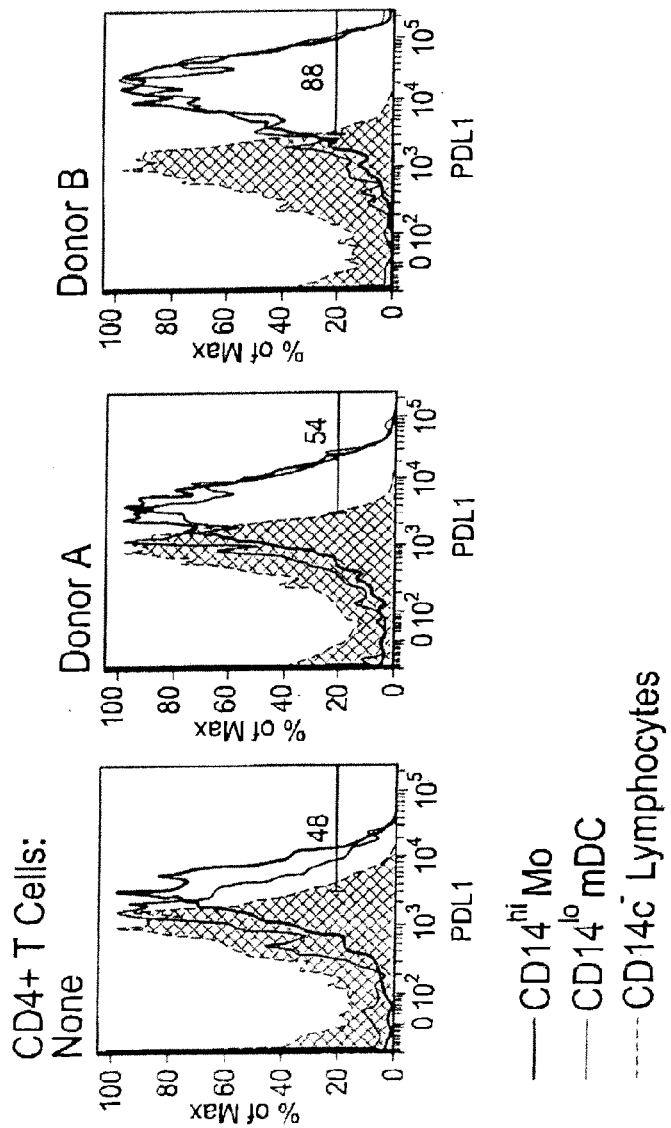
FIG. 16 shows PD-L1 expression is induced in isolated mDC and Mo to the same extent as in mixed PBMC cultures. CD11c+ cells were isolated by FACS to >99% then cultured over night in parallel with unfractionated PBMC from the same subjects. The numbers represent percent of Mo expressing PD-L1.

Consistent with a prior report, we also observed that although Mo populations were fairly homogenous with respect to expression of CD80/CD86, immature mDC segregated into CD80/CD86$^{lo}$ and CD80/CD86$^{hi}$-expressing groups, suggesting differing abilities for T-cell stimulation (FIG. 14). Moreover, in control and SLE remission PBMC, the majority of PD-L1 protein was expressed by CD80/CD86$^{hi}$ mDC, suggesting that T-cell stimulation by these most potent APC is normally held in check by this negative regulator. Surprisingly, the CD80/CD86$^{hi}$ subset of mDC was markedly lacking in SLE flare, although the reasons for this are currently unclear.

The finding of decreased PD-L1 protein during active SLE has significant implications for conversion of APC to a pathological state. Although immature mDC and Mo from children with active SLE failed to up-regulate PD-L1, both cell types retained the ability to express several other markers, including CD80/CD86, at the APC surface. As CD80/CD86-mediated T-effector signaling is normally countered by PD-L1, lupus APC could potentially have an abnormally high capacity for positive T-cell co-stimulation during SLE flare. A hyperstimulatory role for lupus APC is supported by data showing that mDC and Mo from patients with SLE have an increased ability to activate allogenic T-cells.

Not only do DCs depend upon PD-L1 signaling to diminish T-cell stimulation, but negative co-stimulation by PD-L1 is more effective in immature DCs than in mature DCs, suggesting a mechanism for the immunogenic presentation of autoantigens in SLE. Immature mDC ingest apoptotic bodies and cross-present Ags to cytotoxic T-cells, and lack of PD-1 signaling in vivo results in DC-mediated CD8$^+$ T-cell priming rather than tolerization. Therefore, our data may provide a partial explanation for the self-reactivity observed in lupus patients, whereby PD-L1-deficient immature mDC present apoptosis-related antigens in a pro-inflammatory context.

While examining CD80/CD86 expression, it was also noted that the CD80/CD86$^{hi}$ subgroup of mDC was diminished during SLE flare. This is intriguing, as SLE PBMC proliferate poorly in autologous mixed leucocyte reactions (aMLRs), and it has recently been suggested that CD80/CD86$^{hi}$ mDC are integral for T-cell proliferation during aMLRs. The reason behind the loss of these cells in active SLE is unclear, however, and may be related to increased apoptosis or to tissue sequestration—it has been reported that patients with active Class III and IV lupus nephritis have significantly fewer circulating mDC along with a concomitant increase of immature mDC in renal tissues. It would be interesting to determine whether these renal mDC retain the ability to express PD-L1.

In addition to potentially stimulating autoreactive T effector cells, PD-L1-deficient APC may promote abnormal function and/or development of regulatory T lymphocytes (Treg). It has been demonstrated that PD-L1 signaling is necessary for the suppressive activity of classic CD4+ CD25+ Treg in an animal model of GVHD, and that anti-CD3-stimulated naïve CD4þ T cells could be induced to become Tr1-type regulatory cells if co-stimulated with PD-L1-Ig. Although decreased Treg number and function have been reported in human SLE it remains to be determined whether PD-L1 plays any role in Treg-related deficiencies.

The decreased PD-L1 levels observed on APC from patients with active SLE were not likely a result of medication effects, as the use of immunosuppressive agents was comparable between flare and remission groups (Table I). Three of the children with active SLE and low PD-L1 had been newly diagnosed and had never received any immunosuppression. Additionally, all four of the subjects who provided serial samples (FIG. 2G) were on minimally varying medication regimens at the time of their blood draws. Similarly, a prior study of SLE patients revealed no correlation between the use of immunosuppressive agents in vivo and changes in cell surface markers on peripheral blood DC, as well as no significant effect of chloroquine, steroids, 6-mercaptopurine or mycophenolate mofetil on markers of Mo differentiation and maturation in vitro.

In addition to cytokine dysregulation, SLE leucocytes undergo apoptosis at an increased rate, and we did note an inverse correlation between PD-L1 expression and PBMC apoptosis (Table I). Following this lead, we have preliminary data demonstrating that in vitro treatment of PBMC with polycaspase inhibitors not only reduced leucocyte apoptosis, but increased the expression of PD-L1 on mDC and Mo in all cultures (data not shown). These findings suggest a role for caspase activity in the normal regulation of PD-L1 and provide a potential explanation for the loss of this negative co-stimulator on APC from patients with active SLE. In support of this idea, it has been reported that caspase-3 is directly responsible for the decreased CD3$^-$-chain expression on the surface of SLE T cells.

Our findings complement what is already known regarding PD-L1 expression in human disease; levels of PD-L1 are increased on circulating APC from patients with chronic HIV, hepatitis B or hepatitis C infection, and decreased on DC from patients with multiple sclerosis. As preliminary studies in our laboratory have also indicated abnormally low levels of PD-L1 on APC from patients with some other types of active autoimmune disease, we propose that diminished expression of PD-L1 on circulating APC may be a hallmark of active multi-organ autoimmunity, while elevated levels of PD-L1 on circulating APC may be indicative of chronic infection. If verified in larger samples, this distinction may be medically useful, as it is often unclear whether clinical deterioration in SLE patients represents disease flare or infection.

In summary, our findings link active SLE with the inability of peripheral blood APC to express PD-L1, suggesting that PD-L1 may be functionally important in the maintenance of immune tolerance in SLE. Lack of this protein on the surface of immature mDC also suggests a mechanism for the propensity of the immune system to target apoptosis-associated molecules in SLE, as immature mDC typically ingest and present these self-antigens. Given the inverse correlation between PD-L1 and SLE disease activity, future investigations may reveal a role for PD-L1 fusion proteins or other molecules capable of ligating PD-1 in the treatment of SLE or other autoimmune diseases. Larger studies may determine whether intermittent measurements of PD-L1 on circulating APC could provide an additional tool for monitoring the clinical course of SLE. The above experiments showed that both immature mDC and Mo from children with SLE failed to up-regulate PD-L1 normally, and that this deficiency was associated with increased disease activity.

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer and primates. The most preferred animal is human.

As used herein, the terms "treat" "treating" and "treatment" include "prevent" "preventing" and "prevention" respectively. As used herein, the term "autoimmune disease" includes "immune-related disease," "autoimmune disorder," "immunologic disorder" and "immune-related disorder." As used herein, the term "isolated" refers to materials, such as cells or antibodies, which are removed from at least some of the components that normally accompany or interact with the materials in a naturally occurring environment such that they have been altered, "by the hand of man" from their natural state to a level of isolation or purity that does not naturally occur.

In some other embodiments, the treatments described herein may be administered alone or in combination with another therapeutic compound. Any therapeutic compound used in treatment of the target autoimmune disease can be used.

Many different modes and methods of administration of the therapeutic molecules are contemplated. In some embodiments, delivery routes include, for example, intravenous, intraperitoneal, inhalation, intramuscular, subcutaneous, nasal and oral administration or any other delivery route available in the art. Depending on the particular administration route, the dosage form may be, for example, solid, semisolid, liquid, vapor or aerosol preparation. The dosage form may include, for example, those additives, lubricants, stabilizers, buffers, coatings, and excipients available in the art of pharmaceutical formulations. In some embodiments, gene therapy is utilized to deliver therapeutic molecules to the patient.

Many pharmaceutical formulations are contemplated. In some embodiments, the pharmaceutical formulations can be prepared by conventional methods using the following pharmaceutically acceptable vehicles or the like: excipients such as solvents (e.g., water, physiological saline), bulking agents and filling agents (e.g., lactose, starch, crystalline cellulose, mannitol, maltose, calcium hydrogenphosphate, soft silicic acid anhydride and calcium carbonate); auxiliaries such as solubilizing agents (e.g., ethanol and polysolvates), binding agents (e.g., starch, polyvinyl pyrrolidine, hydroxypropyl cellulose, ethylcellulose, carboxymethyl cellulose and gum arabic), disintegrating agents (e.g., starch and carboxymethyl cellulose calcium), lubricating agents (e.g., magnesium stearate, talc and hydrogenated oil), stabilizing agents (e.g., lactose, mannitol, maltose, polysolvates, macrogol, and polyoxyethylene hydrogenated castor oil), isotonic agents, wetting agents, lubricating agents, dispersing agents, buffering agents and solubilizing agents; and additives such as antioxidants, preservatives, flavoring and aromatizing agents, analgesic agents, stabilizing agents, coloring agents and sweetening agents.

If necessary, glycerol, dimethyacetamide, 70% sodium lactate, surfactants and alkaline substances (e.g., ethylenediamine, ethanol amine, sodium carbonate, arginine, meglumine and trisaminomethane) can also be added to various pharmaceutical formulations.

In the context of some embodiments, the dosage form can be that for oral administration. Oral dosage compositions for small intestinal delivery include, for example, solid capsules as well as liquid compositions which contain aqueous buffering agents that prevent the expanded $T_{reg}$ cell population or other ingredients from being significantly inactivated by gastric fluids in the stomach, thereby allowing the expanded $T_{reg}$ cell population to reach the small intestines. Examples of such aqueous buffering agents which can be employed in the present invention include, for example, bicarbonate buffer at a pH of from about 5.5 to about 8.7. Tablets can also be made gastroresistent by the addition of, e.g., cellulose acetate phthalate or cellulose acetate terephthalate.

EQUIVALENTS

The foregoing written specification is considered to be sufficient to enable one skilled in the art to practice the invention. The foregoing description details certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A kit comprising:
   (i) a detectably labeled antibody specific for PD-L1 for use in determining a PD-L1 level in a blood sample obtained from a human individual; and
   (ii) at least one antibody specific for a cell surface marker of a monocyte or a dendritic cell.

2. The kit of claim 1, wherein the antibody specific for PD-L1 is fluorescently-labeled.

3. The kit of claim 1, wherein the blood sample comprises peripheral blood lymphocytes.

4. The kit of claim 1, wherein the PD-L1 level is the amount of PD-L1 in immature myeloid dendritic cells (mDC) or monocytes in the blood sample.

5. The kit of claim 1, wherein the PD-L1 level is the number of immature mDC or monocytes in the blood sample that express PD-L1.

6. The kit of claim 5, wherein the monocytes comprise CD14+/CD11c+ monocytes.

7. The kit of claim 5, wherein the immature mDCs comprise $CD14^{-/LO}$/CD11c+ mDCs.

8. The kit of claim 1, wherein the human individual has rheumatoid arthritis (RA) or systemic lupus erythematosus (SLE).

9. A kit comprising:
   (i) a detectably labeled antibody specific for PD-L1 for use in determining a PD-L1 level in a blood sample obtained from a human individual; and
   (ii) at least one antibody specific for a cell surface marker selected from the group of CD11c and CD14.

10. The kit of claim 9, wherein the cell surface marker is CD11c.

11. The kit of claim 9, wherein the cell surface marker is CD14.

12. The kit of claim 9, wherein the antibody specific for PD-L1 is fluorescently-labeled.

13. The kit of claim 9, wherein the blood sample comprises peripheral blood lymphocytes.

14. The kit of claim 9, wherein the PD-L1 level is the amount of PD-L1 in immature mDC or monocytes in the blood sample.

15. The kit of claim 9, wherein the PD-L1 level is the number of immature mDC or monocytes in the blood sample that express PD-L1.

16. The kit of claim 15, wherein the monocytes comprise CD14+/CD11c+ monocytes.

17. The kit of claim 15, wherein the immature mDCs comprise $CD14^{-/LO}$/CD11c+ mDCs.

18. The kit of claim 9, wherein the human individual has RA or SLE.

* * * * *